(12) United States Patent
Kawashima et al.

(10) Patent No.: US 7,662,631 B2
(45) Date of Patent: Feb. 16, 2010

(54) SAMPLE ANALYZERS, BACTERIA ANALYZERS, AND SOLUTIONS FOR DILUTING AND CLEANING

(75) Inventors: Yasuyuki Kawashima, Kobe (JP); Masayuki Ikeda, Kobe (JP)

(73) Assignee: Sysmex Corporation, Kobe (JP)

( * ) Notice: Subject to any disclaimer, the term of this patent is extended or adjusted under 35 U.S.C. 154(b) by 258 days.

(21) Appl. No.: 10/692,554

(22) Filed: Oct. 24, 2003

(65) Prior Publication Data

US 2004/0096931 A1     May 20, 2004

(30) Foreign Application Priority Data

Oct. 25, 2002     (JP)     ............... 2002-310585

(51) Int. Cl.
*G01N 35/02*     (2006.01)
(52) U.S. Cl. .......................... 436/49; 436/50
(58) Field of Classification Search ............... 422/68.1, 422/82.05, 67; 436/49, 50, 51, 55
See application file for complete search history.

(56) References Cited

U.S. PATENT DOCUMENTS

| | | | | |
|---|---|---|---|---|
| 5,289,385 | A | * | 2/1994 | Grandone ..................... 702/19 |
| 5,631,165 | A | * | 5/1997 | Chupp et al. .................. 436/43 |
| 6,043,205 | A | | 3/2000 | Hoshiko et al. |
| 6,114,292 | A | * | 9/2000 | Hoshiko et al. ............. 510/161 |
| 2002/0076743 | A1 | | 6/2002 | Sakai et al. |

FOREIGN PATENT DOCUMENTS

| | | |
|---|---|---|
| DE | 43 14 180 A1 | 11/1993 |
| EP | 0 919 609 A1 | 6/1999 |
| EP | 1 004 880 A2 | 5/2000 |
| EP | 1 087 231 A2 | 3/2001 |
| EP | 1 136 563 A2 | 9/2001 |
| JP | 5-001983 | 1/1993 |
| JP | 6-15772 | 3/1994 |
| JP | 11-271331 | 10/1999 |
| JP | 2000-321270 | 11/2000 |

OTHER PUBLICATIONS

"User Guide for ZipTip $_{MC}$: Pipette Tips for Phosphopeptide Enrichment"; Retrieved from Internet Website: www.millipore.com on Apr. 1, 2004; two pages.

* cited by examiner

*Primary Examiner*—Jill Warden
*Assistant Examiner*—Natalia Levkovich
(74) *Attorney, Agent, or Firm*—Brinks Hofer Gilson & Lione

(57) ABSTRACT

Sample analyzers for analyzing a sample are described that include a pipette for suctioning the sample; a sample preparation unit for preparing a measured sample by diluting the sample supplied by the pipette with an acidic solution; a pipette washing unit for washing the pipette with the acidic solution; a detection unit for obtaining a detection signal from the measured sample prepared by the sample preparation unit; and a controller for calculating an analysis result from the detection signal obtained by the detection unit. Bacteria analyzers for analyzing bacteria and solutions for use in sample analyzers are also described.

15 Claims, 24 Drawing Sheets

SAMPLE ANALYZERS, BACTERIA ANALYZERS, AND SOLUTIONS FOR DILUTING AND CLEANING

RELATED APPLICATIONS

This application claims priority under 35 U.S.C. §119 to Japanese Patent Application No. 2002-310585, filed Oct. 25, 2002.

FIELD OF THE INVENTION

The present invention relates to sample analyzers provided with a pipette for suctioning samples, and to processing solutions for diluting and cleaning.

BACKGROUND

A urine analyzer provided with a washing means for washing a urine flow path is known, which includes a nozzle. After urine has been suctioned for examination from the nozzle and the urine has been completely titrated from the nozzle to a reagent pipette, the urine is examined based on the reaction in the reagent pipette. The urine analyzer is further provided with a concentration detection means for detecting the concentration of a specific component contained in the urine suctioned from the nozzle, and a washing capacity control means for varying the washing capacity of the washing means based on the detection result of the concentration detection means (for example, Japanese Laid-Open Patent Publication No. 2000-321270).

A washing device for a dispensation injection nozzle is known that is provided with an ultrasonic wave generating means for generating ultrasonic wave vibrations while optionally changing the position of the node on the dispensation injection nozzle without generating a node of the ultrasonic vibration in the dispensation injection nozzle that suctions and discharges a sample. The dispensation injection nozzle is vibrated to dislodge sample adhered to the inner surface and outer surface of the dispensation injection nozzle from the dispensation injection nozzle (for example, Japanese Laid-Open Patent Publication No. H5-1983).

A pipette washing device provided with a trough for accommodating water for washing is known provided with a brush arranged inside the trough, a magnetic body mounted on the bottom part of the brush, a rotating magnetic body having the same polarity as the magnetic body mounted on the bottom of the brush, and a drive means for rotating the rotating magnetic body (for example, Japanese Utility Model Publication No. H6-15772).

In sample analyzers which suction a sample from a nozzle (pipette) such as those described above, the nozzle must be washed before suctioning the next sample. Analysis of the next sample may be adversely affected if the nozzle is inadequately washed.

To solve this problem, in the urine analyzer disclosed in the above-mentioned Japanese Patent Publication No. 2000-321270, the number of washings or the amount of washing fluid used is changed in accordance with the detection result obtained by the concentration detection means. However, if the number of washings is increased, the processing capability of the device is markedly reduced. If the amount of washing fluid used is increased, the operating cost of the device is increased. Furthermore, this urine analyzer is provided with a concentration detection means for changing the washing capability, which also increases the size of the device.

The devices disclosed in Japanese Laid-Open Patent Publication No. H5-1983 and Japanese Utility Model Publication No. H6-15772 also result in larger devices similar to the device described in Japanese Patent Publication No. 2000-321270.

SUMMARY

The scope of the present invention is defined solely by the appended claims, and is not affected to any degree by the statements within this summary.

A sample analyzer embodying features of the present invention for analyzing a sample includes: a pipette for suctioning the sample; a sample preparation unit for preparing a measured sample by diluting the sample supplied by the pipette with an acidic solution; a pipette washing unit for washing the pipette with the acidic solution; a detection unit for obtaining a detection signal from the measured sample prepared by the sample preparation unit; and a controller for calculating an analysis result from the detection signal obtained by the detection unit.

A bacteria analyzer embodying features of the present invention for analyzing a bacterium in a sample includes: a pipette for suctioning the sample; a sample preparation unit for preparing a measured sample from the sample supplied by the pipette; a pipette washing unit for washing the pipette with an acidic solution; a detection unit for obtaining a detection signal from the measured sample prepared by the sample preparation unit; and a controller for calculating an analysis result from the detection signal obtained by the detection unit.

A solution embodying features of the present invention includes: a solvent; and an acidic buffering agent. The solution is acidic and the solution is used for diluting and cleaning in a sample analyzer that analyzes a predetermined component included in a sample.

DETAILED DESCRIPTION

The present invention provides a sample analyzer which improves washing capability without reducing the processing capability of the device, without increasing the amount of washing fluid used, and without increasing the size of the device.

An embodiment of the present invention is described hereinafter in reference to the drawings. The present invention is not limited to this representative description. This embodiment of the sample analyzer is a bacteria analyzer for counting the number of bacteria in a sample (urine).

The structure of various parts of the sample analyzer are described below.

Sample Preparation Device

Figure 1:
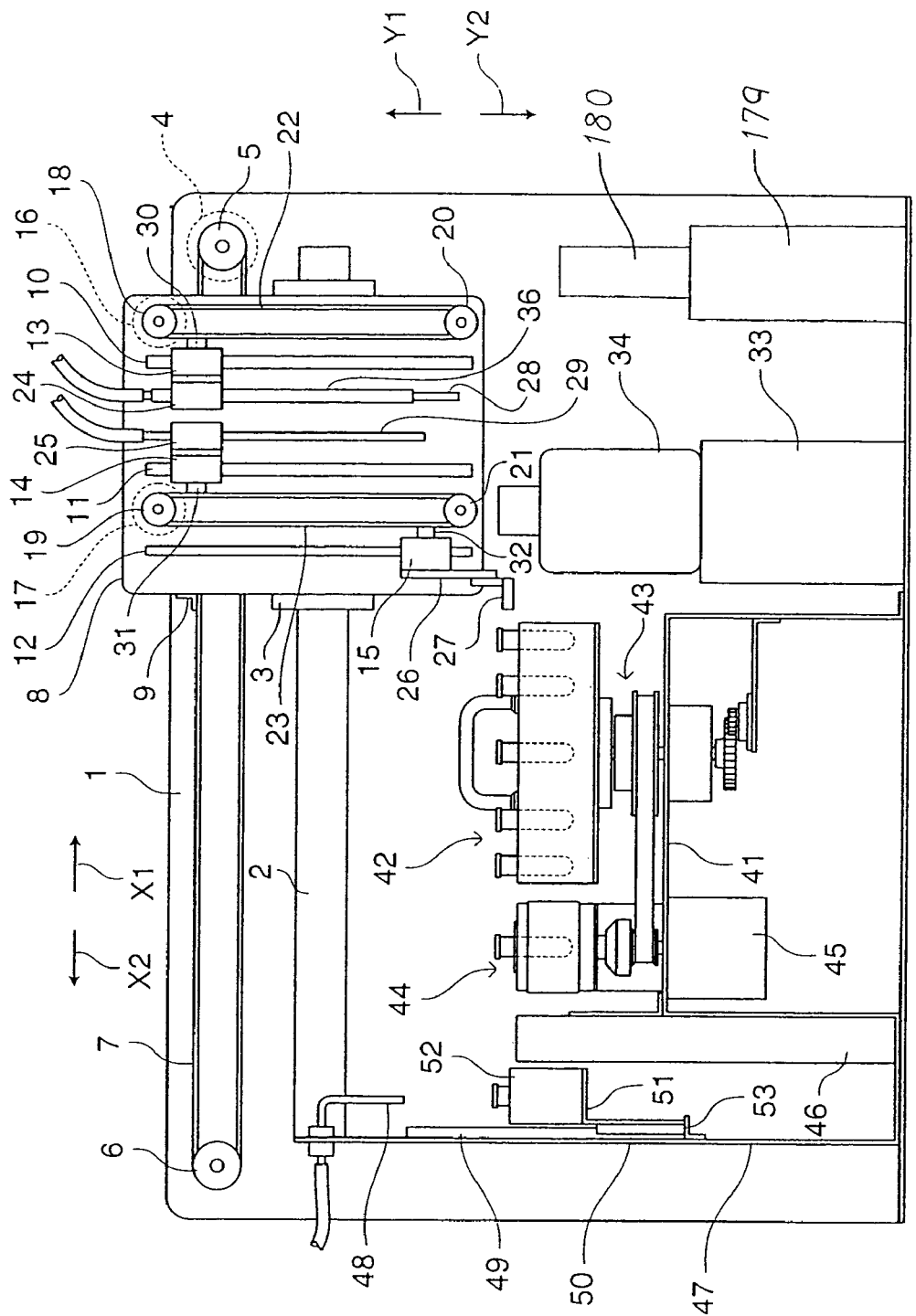
FIG. 1 shows a front view of a sample preparation device embodying features of the present invention.

FIG. 1 shows a front view of an embodiment of the sample preparation device of the present invention.

A slide rail 2 is provided horizontally to a main frame 1 as shown in the drawing, and a slide element 3 is supported by the slide rail 2 so as to be slidable in a horizontal direction.

The main frame 1 supports a drive pulley 5 driven by a stepping motor 4, and supports a corresponding driven pulley 6 so as to be rotatable. A timing belt 7 is supported between the pulleys 5 and 6 so as to be parallel to the slide rail 2. The slide element 3 is provided with a horizontally movable plate 8, and the plate 8 is connected to the timing belt 7 via a connector 9. When the stepping motor 4 rotates, the plate 8 is moved in the arrow X1 direction or the arrow X2 direction in accordance with the motor rotation direction.

Three slide rails 10, 11, and 12 are provided in a perpendicular direction relative to the plate 8, and the slide rails 10, 11, and 12, respectively, support slide elements 13, 14, and 15 so as to be slidable in a perpendicular direction.

The plate 8 supports the drive pulleys 18 and 19, which are respectively driven by the stepping motors 16 and 17, and supports the corresponding driven pulleys 20 and 21 so as to be rotatable. Timing belts 22 and 23 are respectively supported between pulleys 18 and 20 and pulleys 19 and 21 in a perpendicular direction.

The slide elements 13 and 14 are provided with a first pipette 28 and a second pipette 29 through the respective support members 24 and 25, and the slide element 15 is provided with a catcher 27 through the support member 26. The first pipette 28 is provided with an external pipette heater 36, which heats the suctioned fluid to 42° C.

The slide element 13 is connected to the timing belt 22 via a connector 30, and the slide elements 14 and 15 are connected to the timing belt 23 via the connectors 31 and 32, respectively. When the stepping motor 16 rotates, the first pipette 28 is moved in the arrow Y1 direction or the arrow Y2 direction in accordance with the motor rotation direction. When the stepping motor 17 rotates, the second pipette 29 and the catcher 27 are moved in the arrow Y1 direction or the arrow Y2 direction in accordance with the motor rotation direction.

The support frame 41 is provided with a turntable 42, turntable rotation mechanism 43, mixing container rotation mechanism 44, stepping motor 45 as a rotation drive source, and container discard unit 46. A third pipette 48 is fixedly attached to the support frame 47, and a slide rail 49 is fixedly attached to the support frame 47 in a perpendicular direction. The slide rail 49 supports a slide element 50 so as to be slidable in a perpendicular direction.

The slide element 50 is provided with a washing unit 52 through the support member 51. A stopper 53 is provided below the support frame 47, to stop the slide element 50 at the position shown in FIG. 1, such that the slide element 50 does not move below the slide rail 49. A table 33 is provided to the right of the support frame 41, and a dilution solution container 34 is installed on top of the table 33. A table 179 is provided to the right of the table 33, and a washing chamber 180 is provided on top of the table 179.

Figure 2:
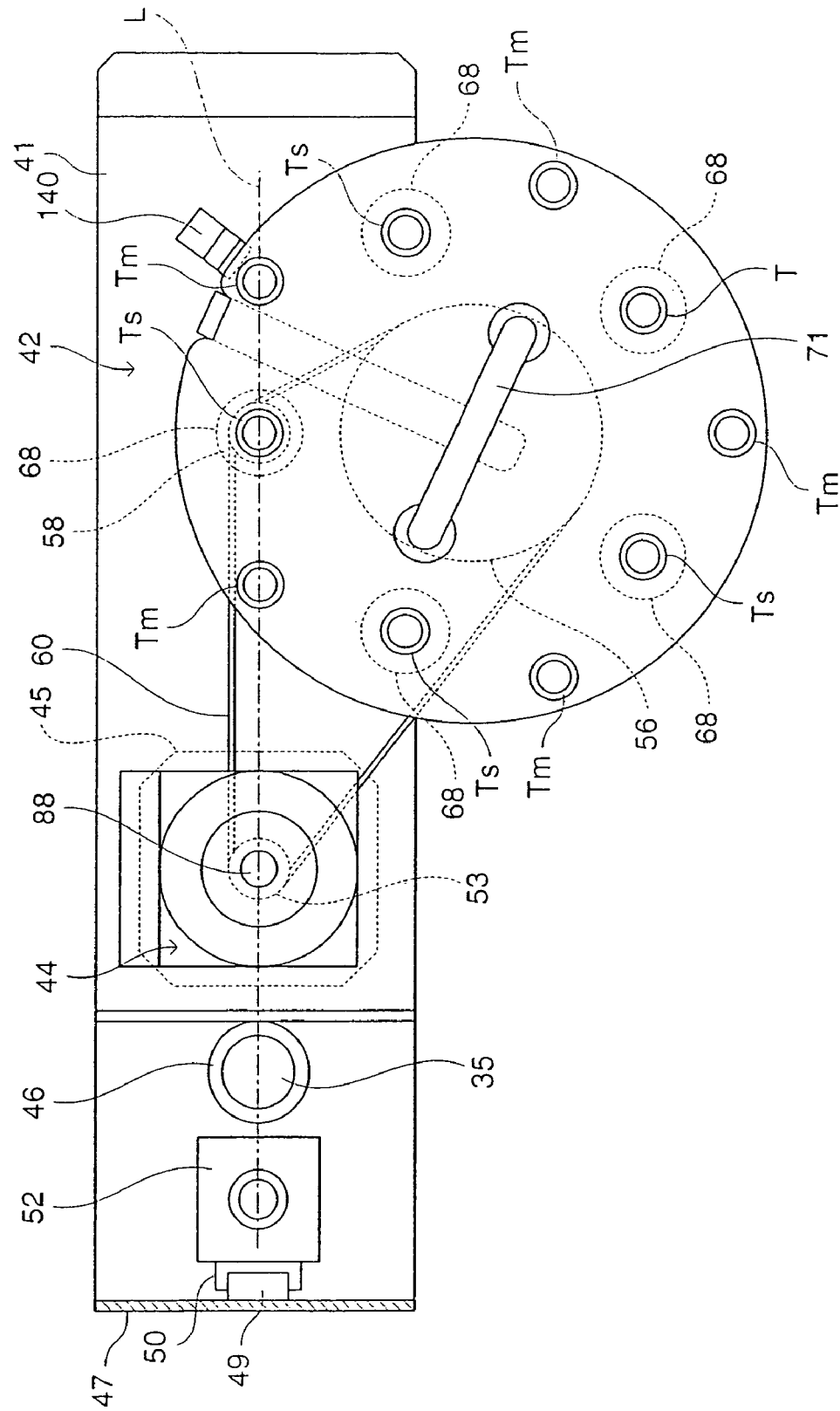
FIG. 2 shows a top view of a portion of the device shown in FIG. 1.
Figure 3:
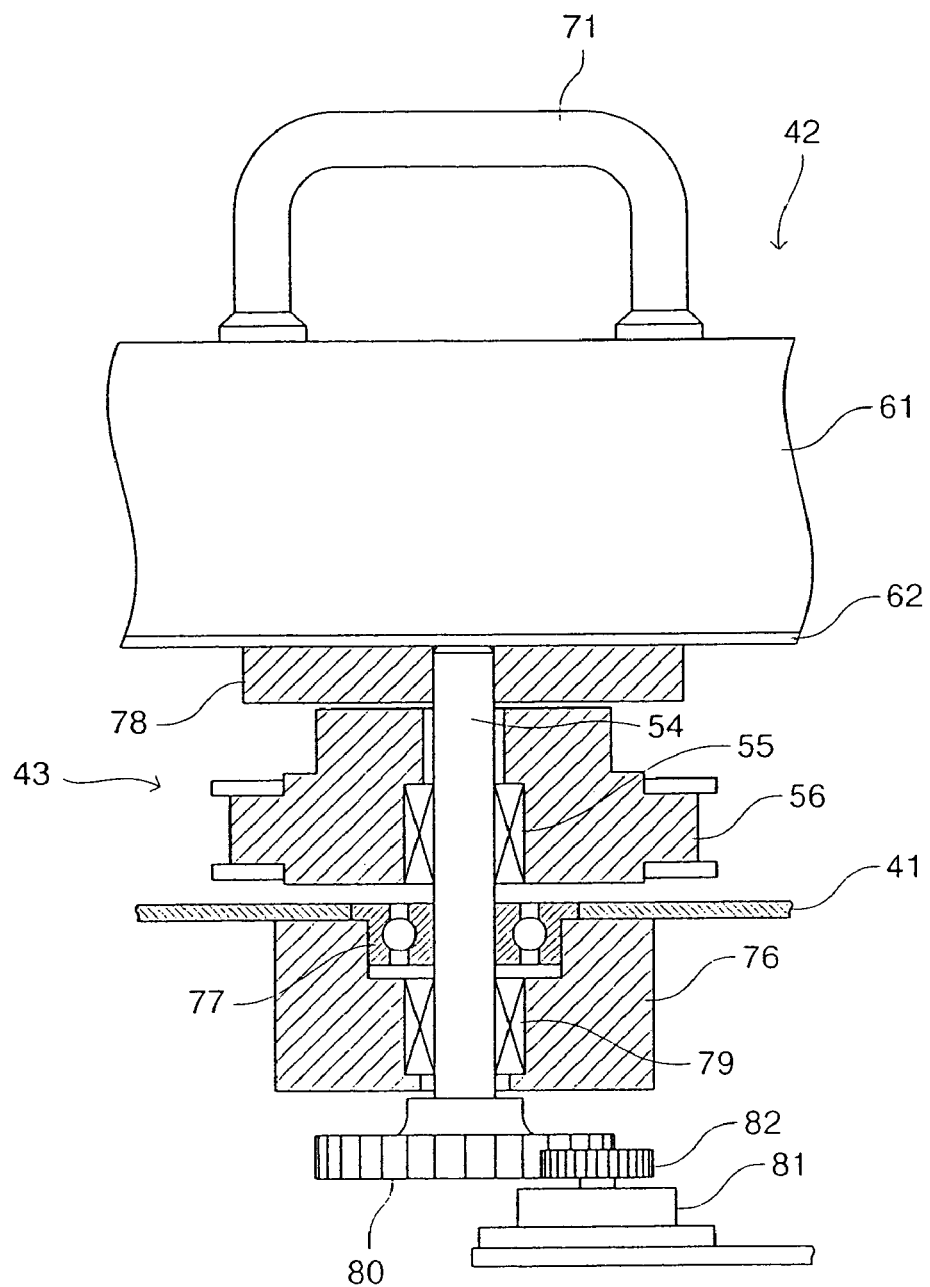
FIG. 3 shows a longitudinal sectional view of the portion of the device shown in FIG. 2
Figure 4:
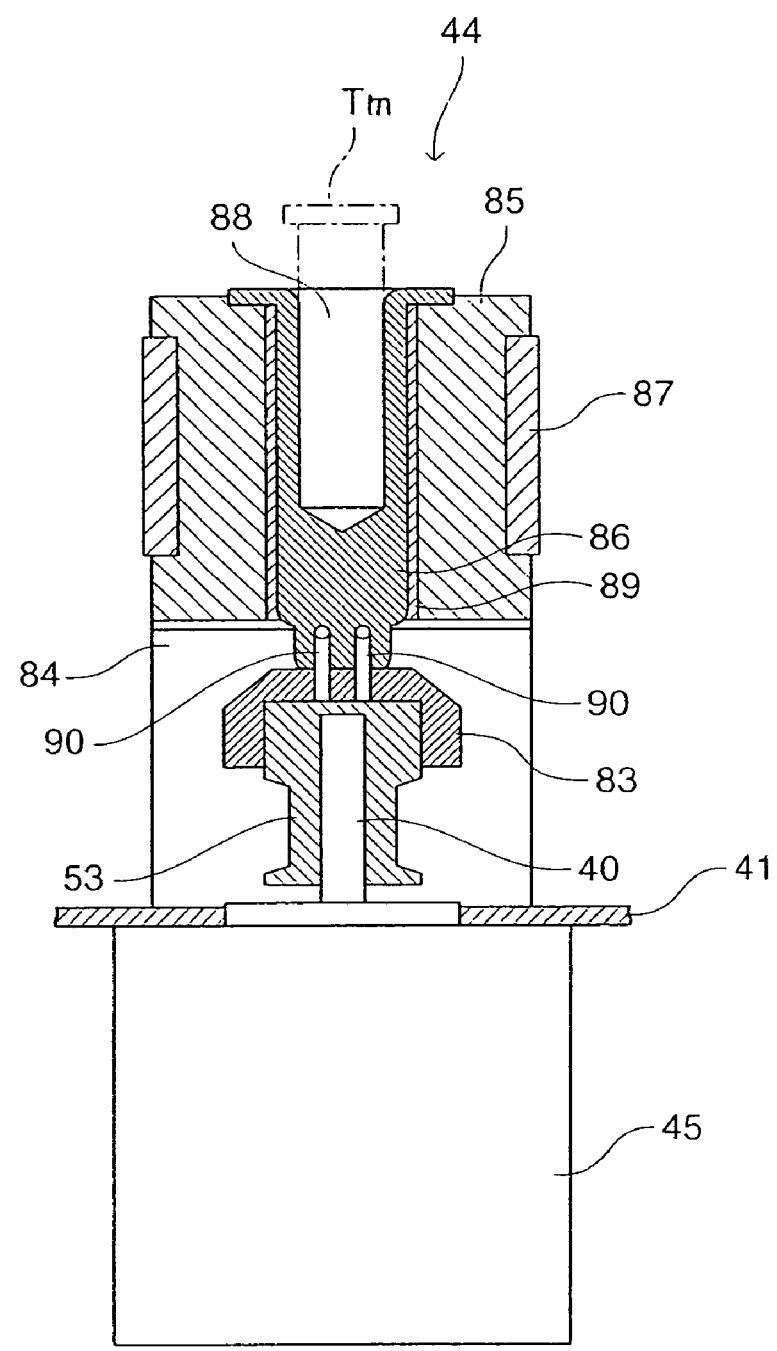
FIG. 4 shows a longitudinal sectional view of the portion of the device shown in FIG. 2.

FIG. 2 shows a top view of the support frame 41. FIG. 3 shows a longitudinal section view of the turntable rotation mechanism 43. FIG. 4 shows a longitudinal section view of the mixing container rotation mechanism 44.

As shown in FIG. 4, a pulley 53 is connected to the output shaft 40 of the stepping motor 45. As shown in FIG. 3, a pulley 56 is connected via a one-way clutch 55 to the drive shaft 54 of the turntable 42.

Figure 5:
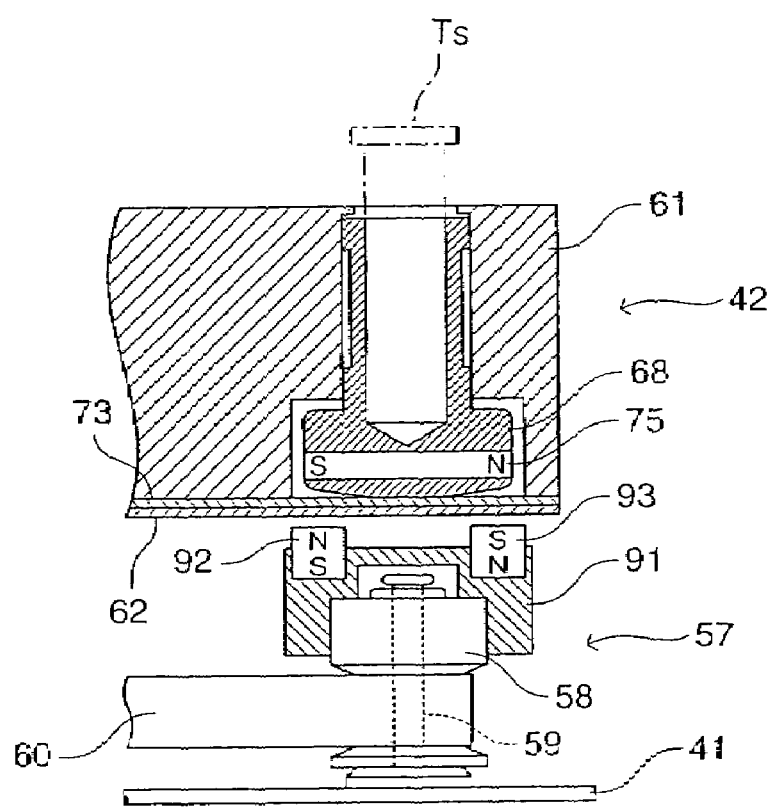
FIG. 5 shows a longitudinal sectional view of the portion of the device shown in FIG. 2.

As shown in FIG. 5, a sample container rotation mechanism 57 is provided between the turntable 42 and the support frame 41, and the rotation mechanism 57 has a pulley 58 supported by a shaft 59 on the support frame 41 so as to be rotatable.

As shown in FIG. 2, the pulleys 53, 56, and 58 are connected by a single timing belt 60. Accordingly, the rotational force of the stepping motor 45 is transmitted to the mixing container rotation mechanism 44 (FIG. 4), and at the same time is also transmitted to the turntable rotation mechanism 43 (FIG. 3) and sample container rotation mechanism 57 (FIG. 5) through the timing belt 60 and the pulleys 53, 56, and 58.

The third pipette 48, washing unit 52, container discard unit 46, pulley 53, pulley 58, and washing chamber 180 are arrayed in series on the straight line L shown in FIG. 2, and the first pipette 28, second pipette 29, and catcher 27 are provided so as to move on the line L via the drive of the stepping motor 4.

The turntable 42 is constructed so that five sample containers Ts and five empty mixing containers Tm can be installed at equal intervals on concentric circular circumferences having different diameters, and so that one sample container Ts, and two empty mixing containers Tm on either side thereof can be aligned on the line L.

Figure 8:
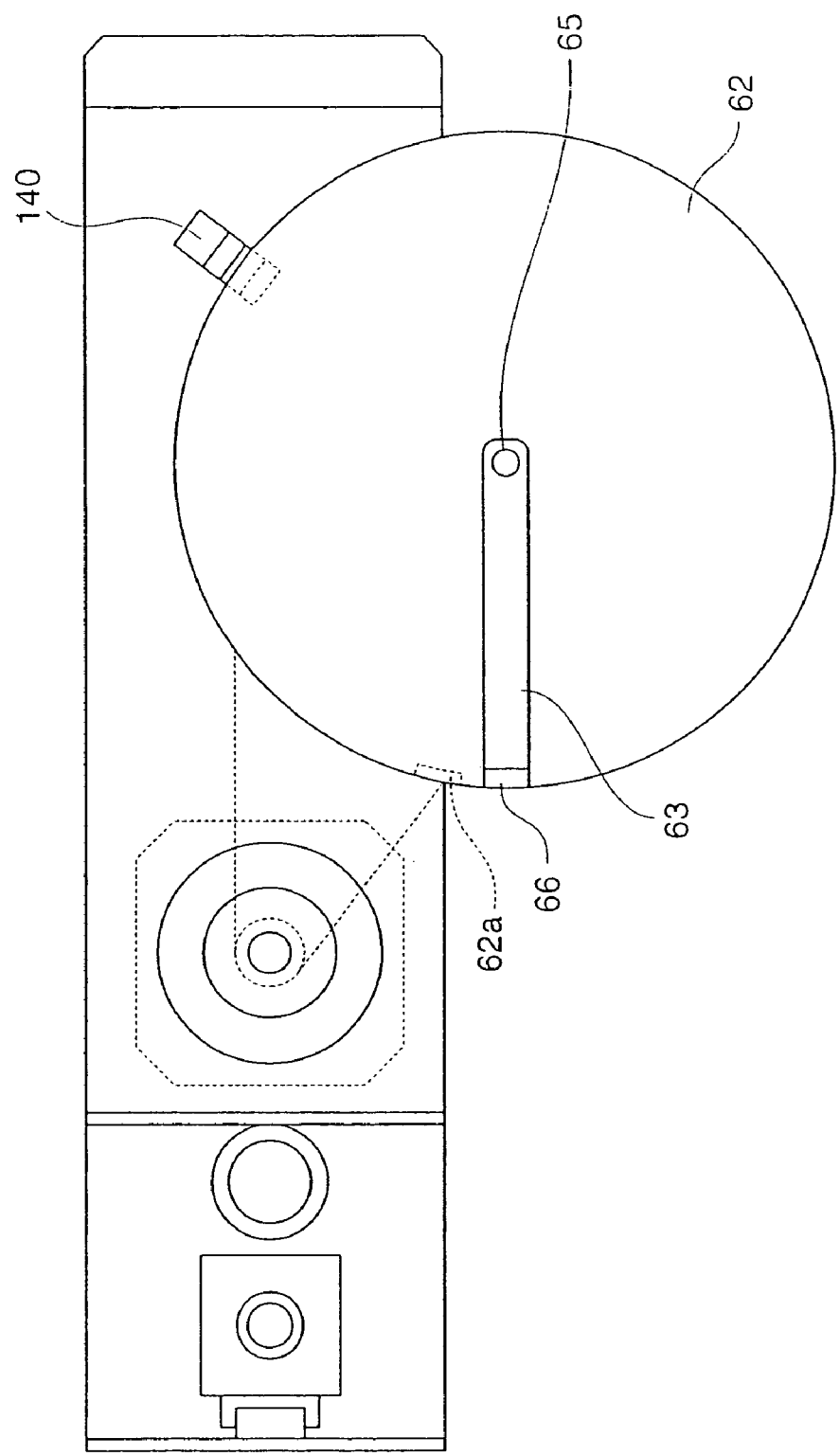
FIG. 8 shows a top view showing the container holder unit removed from the device shown in FIG. 1.
Figure 18:
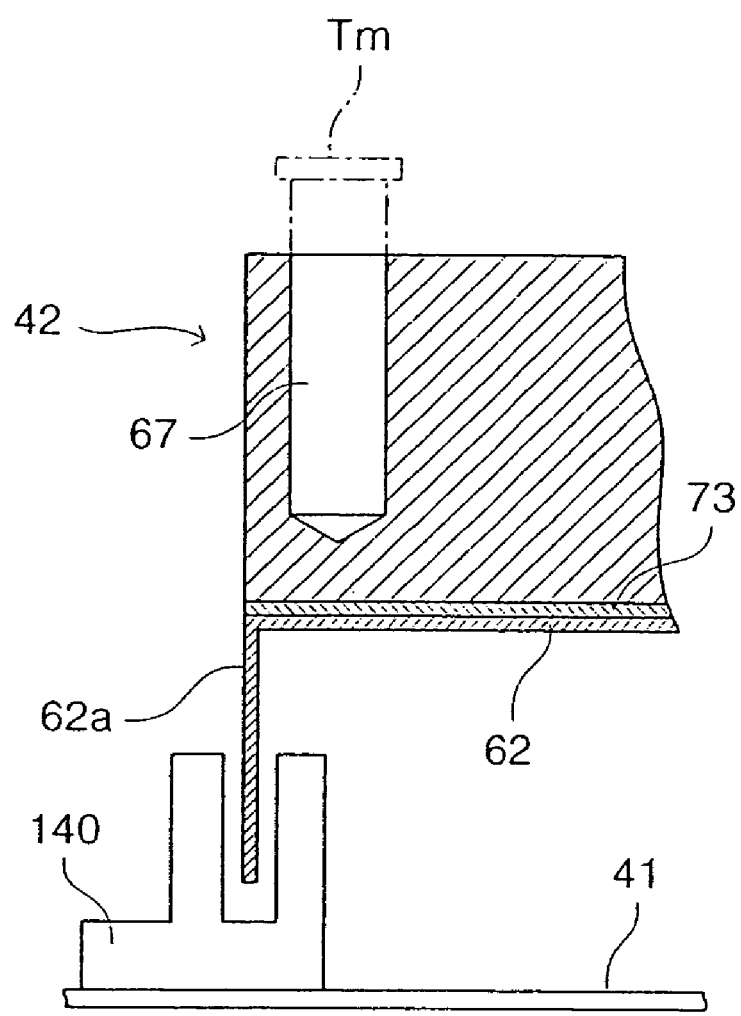
FIG. 18 illustrates the photointerrupter placement in an embodiment of the present invention.

As shown in FIGS. 2, 8, and 18, a photointerrupter 140 is provided on the support frame 1, and a light shield 62a extends below the turntable 42 so as to block the light to the photointerrupter 140. These elements are used to detect a reference position (initial position) of the turntable 42 in a manner described below.

Turntable

Figure 6:
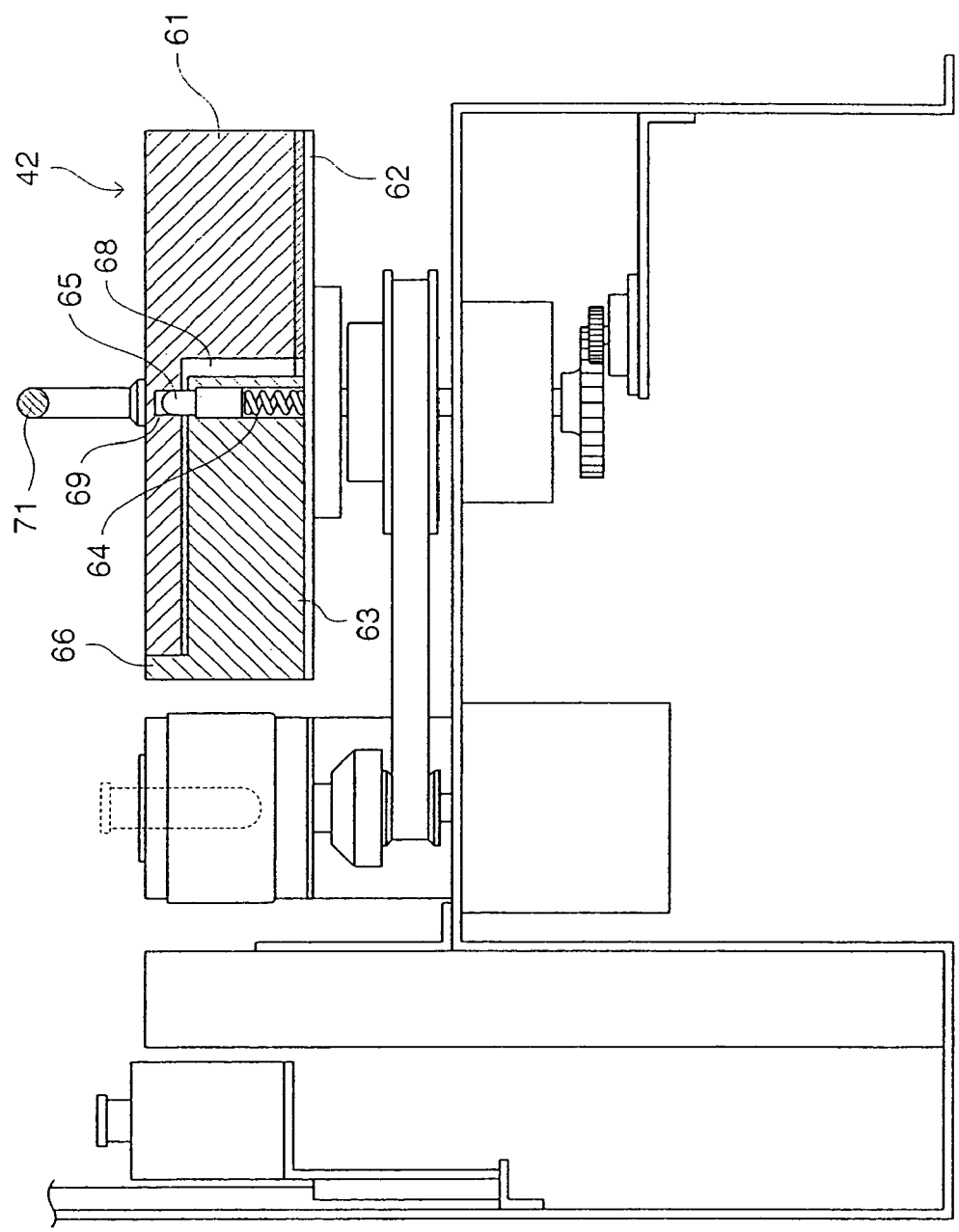
FIG. 6 shows a longitudinal sectional view of the portion of the device shown in FIG. 2.

FIG. 6 shows a structural diagram showing a longitudinal section view of the turntable 42.

Figure 7:
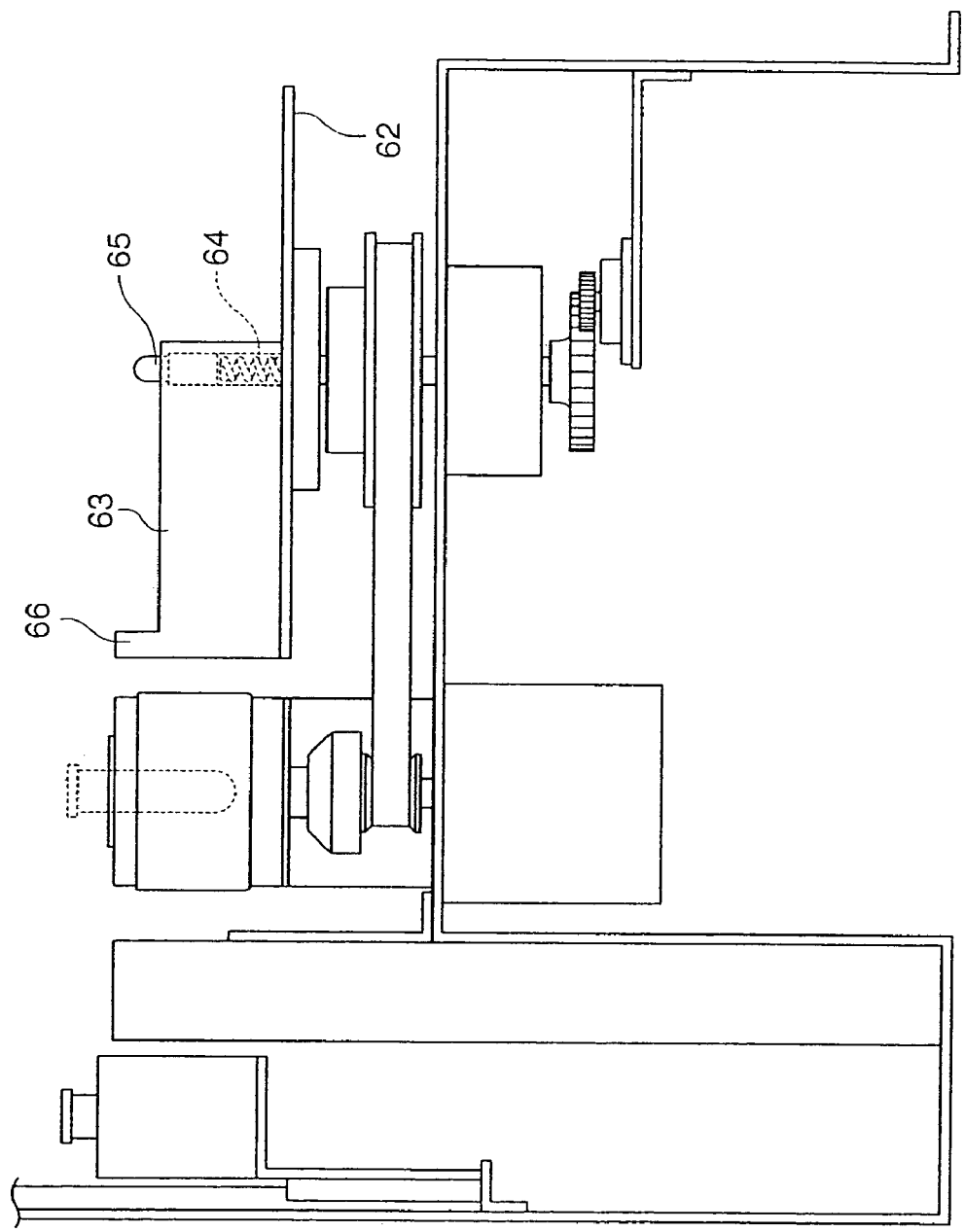
FIG. 7 shows a side view showing the container holder unit removed from the device shown in FIG. 1.

As shown in the drawing, the turntable 42 includes a disk-like container holder 61 formed of resin, and a rotating plate 62 formed of a nonmagnetic material (stainless steel or aluminum) for holding the container holder 61 so as to allow its removal. FIGS. 7 and 8 show, respectively, a side view and a top view of the turntable 42 with the container holder 61 removed from the rotating plate 62.

As shown in these drawings, a guide block 63 is provided on the top surface of the rotating plate 62 to guide the installation of the container holder 61. The guide block 63 is provided with a positioning pin 65 for centering the rotating plate 62, and the positioning pin 65 is forced upward via a compression spring 64. The guide block 63 is also provided with a protrusion 66 for stopping the container holder 61 at the edge position of the rotating plate 62.

Figure 9:
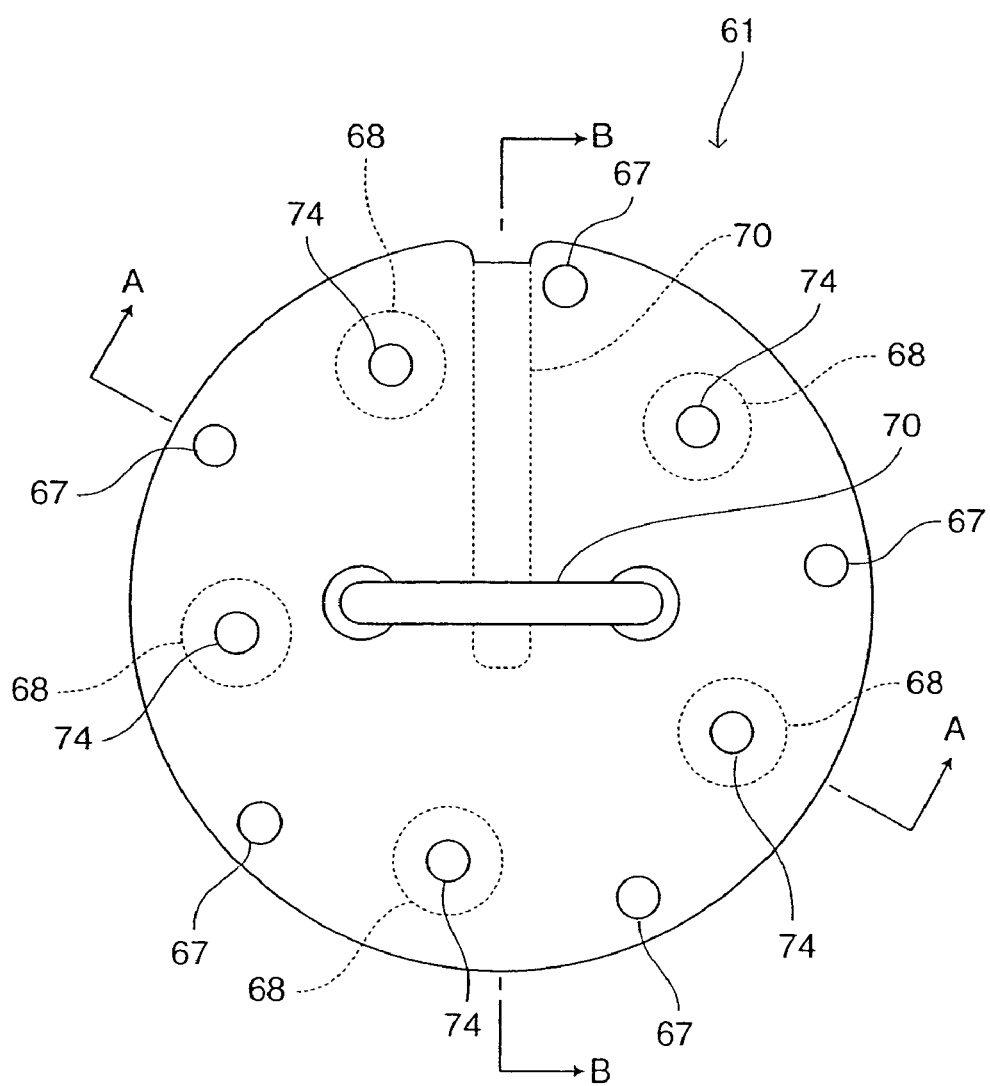
FIG. 9 shows a top view of the container holder unit of the device shown in FIG. 1.
Figure 10:
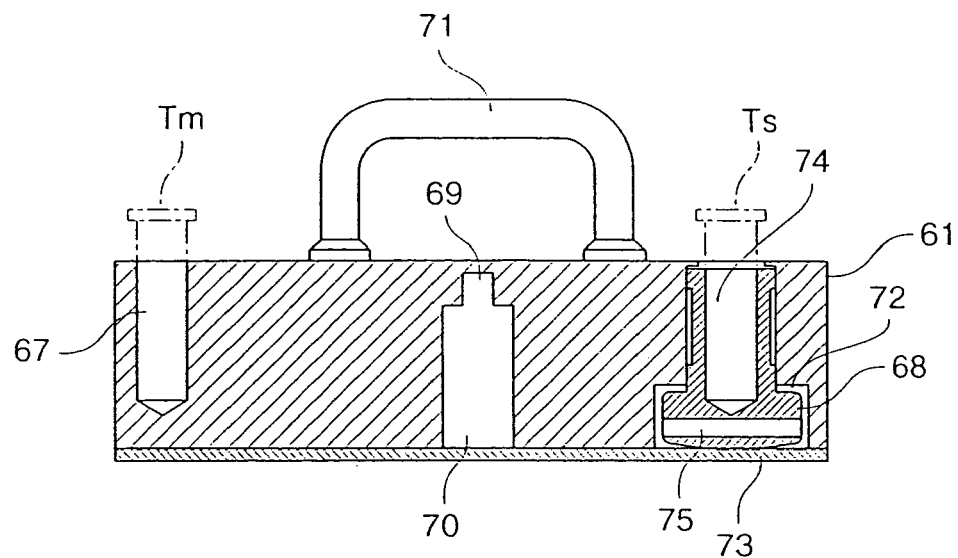
FIG. 10 shows a cross section view along the line A-A of FIG. 9.
Figure 11:
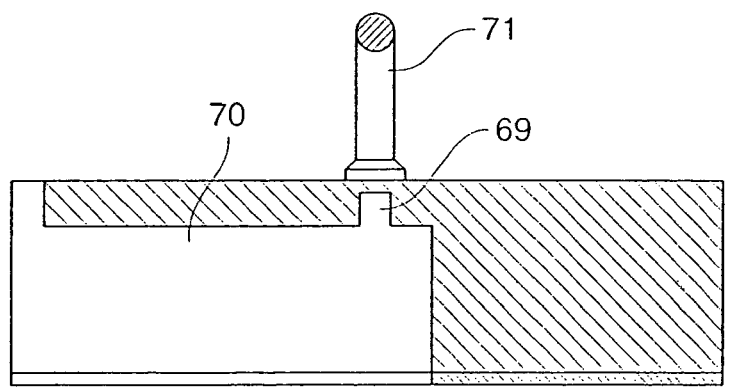
FIG. 11 shows a cross section view along the line B-B of FIG. 9.
Figure 12:
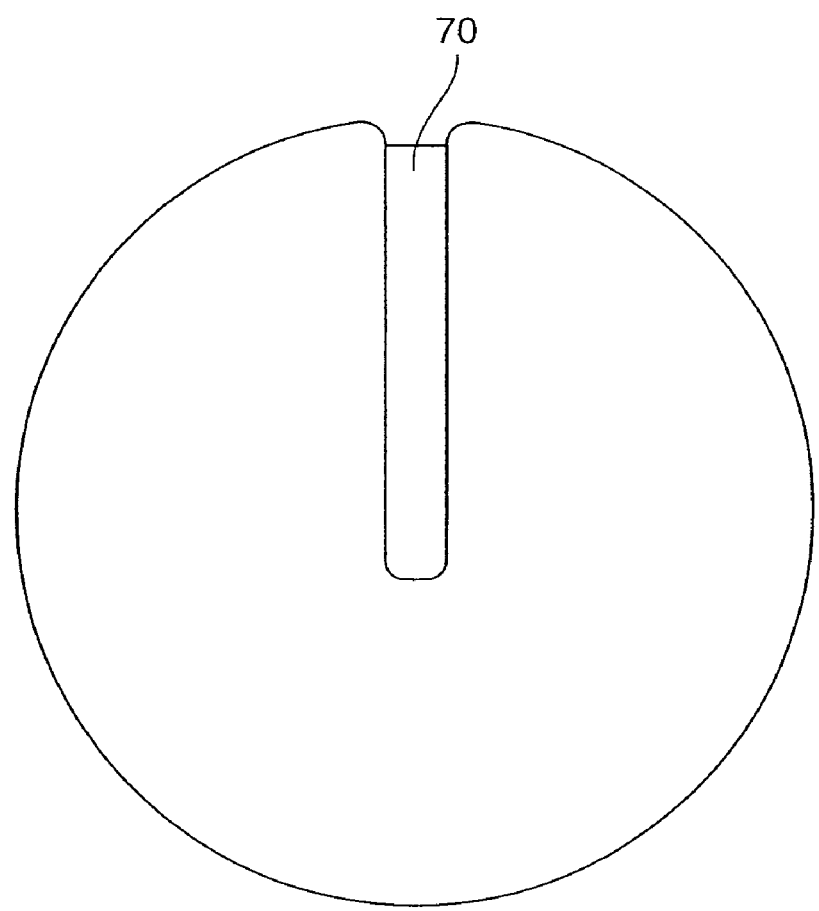
FIG. 12 shows a bottom view of the container holder unit of the device shown in FIG. 1.

FIG. 9 shows a top view of the container holder 61 removed from the rotating plate 62. FIG. 10 shows a cross-sectional view along the line A-A in FIG. 9. FIG. 11 shows a cross-sectional view along the line B-B in FIG. 9. FIG. 12 shows a bottom view of the container holder 61. As shown in FIG. 9, the container holder 61 is provided with five container holes 67 for accommodating the empty mixing containers Tm (FIG. 2), and five first holders 68 for accommodating the sample containers Ts (FIG. 2), which are provided at equal intervals on concentric circular circumferences having different diameters.

As shown in FIGS. 10 and 11, the container holder 61 is provided with a channel 70 which engages the guide block 63 when installed on the rotating plate 62 (FIG. 7). The channel 70 has a positioning hole 69 for accepting the positioning pin 65 at the center of the container holder 61. Furthermore, the top surface of the container holder 61 is provided with a handle 71 used when installing and removing the container holder 61 on the rotating plate 62.

Figure 15:
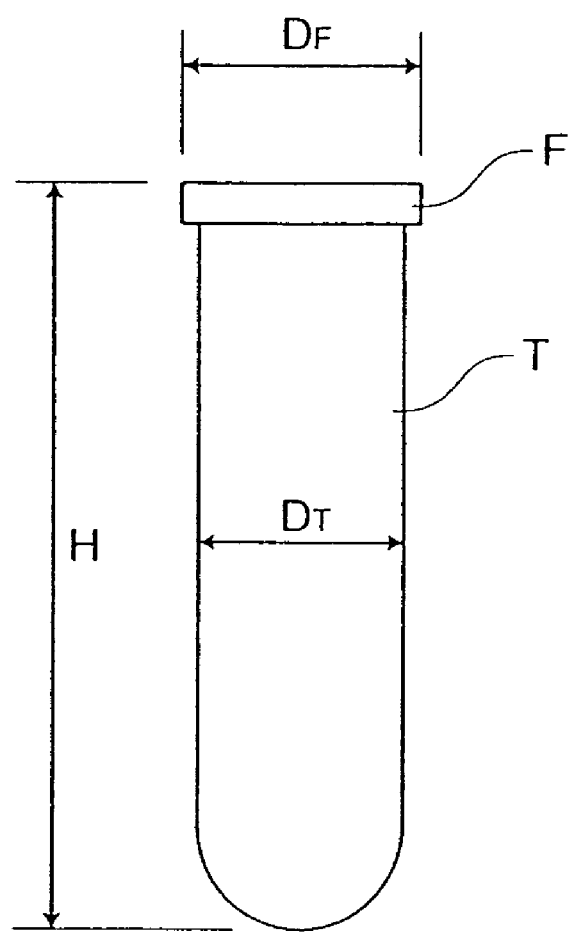
FIG. 15 shows a side view of a disposable container used in the device shown in FIG. 1.

In the sample preparation device of the present embodiment, the disposable container (hereinafter referred to as "tube") T shown in FIG. 15 is used as the sample container Ts for holding a sample collected from a person being tested, and as a mixing container Tm for preparing an analysis sample by mixing the sample and a predetermined fluid.

The tube T is a cylindrical container formed of styrol (transparent) resin preferably with a height dimension H=39.85±0.1 mm, external diameter DT=7.6±8.2 mm, and capacity of approximately 0.7 mL. The tube is provided with a flange F (external diameter DF=10 mm) at the top edge so as to prevent the tube T from falling from the catcher 27 when held by the catcher 27 in a manner described below.

As shown in FIG. 10, the first holder 68 is inserted from the bottom of each of the five cylindrical concavities provided in the container holder 61 and is supported by a bottom plate 73 formed of a nonmagnetic material (e.g., stainless steel or aluminum).

The top of the first holder 68 is provided with a hole 74 for accepting the sample container Ts, and is supported by the outer wall of the concavity 72 so as to be rotatable about an axis. The first holder 68 is also provided with a magnetic rod 75 passing through the bottom of the first holder 68 in a direction intersecting the axis, such that the first holder 68 is rotated about the axis when a rotating magnetic field is introduced from below the bottom plate 73.

Turntable Rotation Mechanism

As shown in FIG. 3, the base end of the drive shaft 54 of the turntable 42 is fixedly attached to the center of the back surface of the rotating plate 62 via a boss 78. The support frame 41 supports a bearing holder 76, and the drive shaft 54 is supported so as to be rotatable by the support frame 41 via a bearing 77 held on the bearing holder 76. The drive shaft 54 is mounted on the bearing holder 76 through a one-way clutch 79.

The one-way clutch 55 is disposed between the pulley 56 and the drive shaft 54 and linked with both as described above. A super gear 80 provided on the tip of the drive shaft 54 engages a super gear 82 provided on the rotating shaft of a damper 81. The damper 81 normally acts on the drive shaft 54 to suppress a flywheel effect through the inertia of the turntable 42, and operates so as to reduce over-rotation particularly when the turntable 42 is stopped.

The operation of the clutches 55 and 79 are described below.

Viewed from the output shaft side, when the stepping motor 45 (FIG. 2) rotates in a clockwise direction causing the pulley 56, viewed from above, to rotate in the clockwise direction, the one-way clutch 55 is ON (operating), and the one-way clutch 79 is OFF (open), such that the turntable 42 receives the action of the damper 81 and rotates in a clockwise direction when viewed from above.

Conversely, when the stepping motor 45 rotates in a counter clockwise direction, the one-way clutch 55 is OFF and the one-way clutch 79 is ON, such that the drive shaft 54 prevents rotation and is locked on the bearing holder 76, and the pulley 56 idles. That is, the turntable 42 can rotate in a clockwise direction only when the stepping motor 45 rotates in a clockwise direction.

Mixing Container Rotation Mechanism

In the mixing container rotation mechanism shown in FIG. 4, a cylindrical holding member 85 is attached to a mounting plate 84 provided above the support frame 41. A through-hole is provided in the holding member 85 to allow the second holder 86 to be received from above, and a film heater 87 is wrapped around the outer surface.

The second holder 86 has a hole 88 for receiving and holding the mixing container Tm from above. The holding member 85 is provided with a thin cylindrical oilless bushing inserted into the through hole, such that the inner surface of the oilless bushing 89 and the outer surface of the second holder 86 are in slidable contact so as to allow the second holder 86 to smoothly rotate about an axis.

A coupling 83 is attached to the top of the pulley 53, and the coupling 83 is provided with two pins 90, which extend upward. The bottom surface of the second holder 86 is provided with two holes, which accommodate the two pins 90. In this way, the second holder 86 is mechanically linked with the pulley 53 so as to be removable. When the stepping motor 45 rotates in either a clockwise direction or a counter clockwise direction, the second holder 86 smoothly rotates in the same direction as the stepping motor 45 about the axis via the oilless bushing 89.

Sample Container Rotation Mechanism

In the sample container rotation mechanism 57 shown in FIG. 5, a cylindrical magnet coupling 91 is attached to the top of the pulley 58, and a pair of rod magnets 92 and 93 are embedded perpendicularly on the magnet coupling 91 disposed about the center of the shaft 59 of the pulley 58. The rod magnet 92 has an N-pole confronting the turntable 42, and the rod magnet 93 has an S-pole confronting the turntable 42.

Since the bottom plate 73 and the rotating plate 62 are formed of nonmagnetic material as described above, when the first holder 68, which is housed in the turntable 42, confronts the magnet coupling 91, the N-pole of the rod magnet 92 is magnetically attracted to the S-pole of the rod magnet 75, and the S-pole of the rod magnet 93 is magnetically attracted to the N-pole of the rod magnet 75. That is, the first holder 68 is magnetically coupled with the pulley 58 through the magnet coupling 91. Accordingly, in this state, when the pulley 58 is rotated in either a clockwise direction or a counter clockwise direction by the stepping motor 45, the first holder 68 is rotated in the same direction as the stepping motor 45 about the center axis of the sample container Ts in accordance with the rotation of the pulley 58.

Catcher

Figure 13:
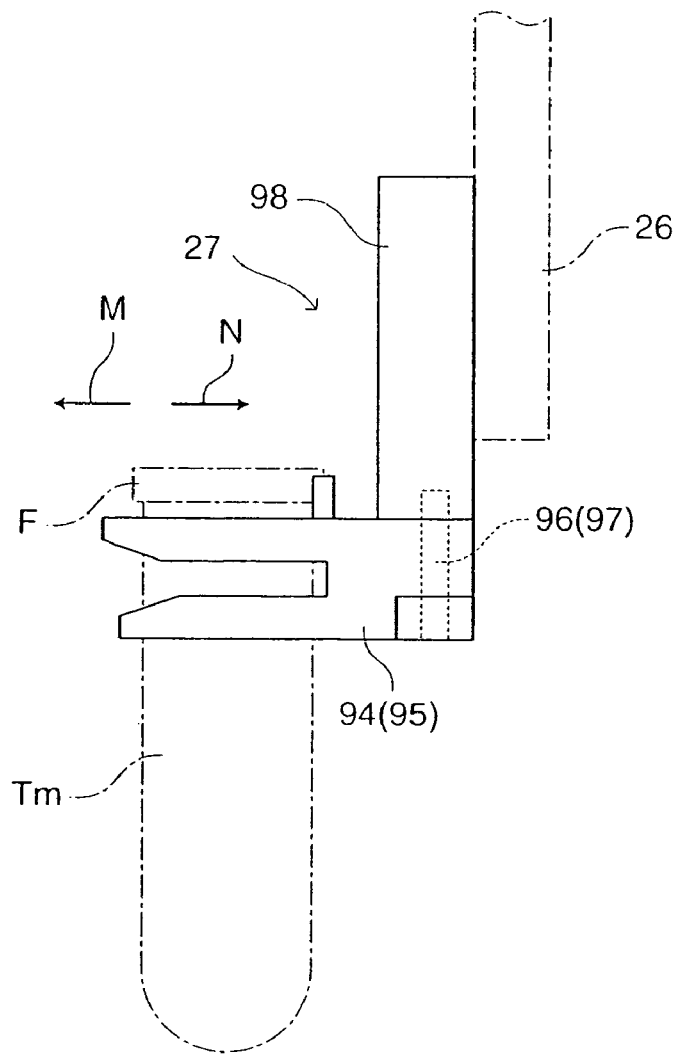
FIG. 13 shows a side view of the catcher of the device shown in FIG. 1.
Figure 14:
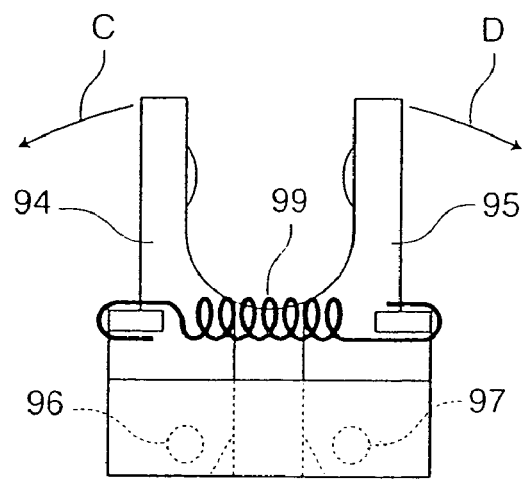
FIG. 14 shows a top view of the catcher of the device shown in FIG. 1.

FIGS. 13 and 14 are a side view and a top view, respectively, of the catcher 27. As shown in these drawings, the catcher 27 is provided with a body 98, and two fingers 94 and 95, and the two fingers 94 and 95 are supported by the body 98 so as to be openable in the arrow C direction and arrow D direction via pins 96 and 97. The fingers 94 and 95 are held in the state shown in FIG. 14 via a force exerted in the closed direction by a tension spring 99.

When the catcher 27 approaches the stationary mixing container Tm in the arrow M direction shown in FIG. 13, the fingers 94 and 95 grip the side surfaces of the mixing container Tm and are stopped by the flange F. With the mixing container Tm in a stationary state, when the catcher 27 moves in the arrow N direction shown in FIG. 13, the catcher 27 separates from the mixing container Tm.

Washing Chamber

Figure 25:
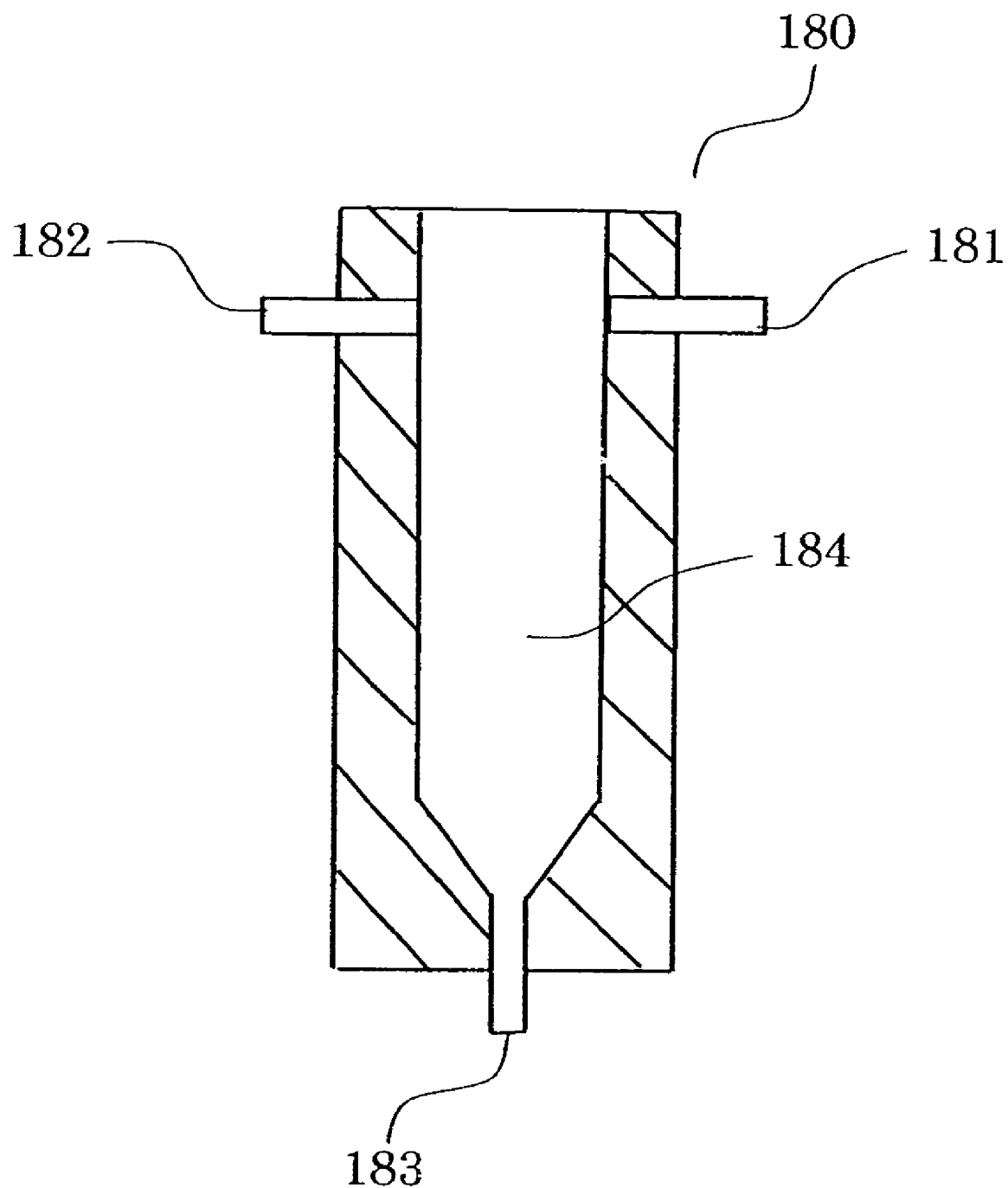
FIG. 25 shows a longitudinal view of the washing chamber in an embodiment of the present invention.

FIG. 25 shows a cross-sectional view of the washing chamber 180 shown in FIG. 1. The washing chamber 180 is provided with a receptacle 184 for receiving sheath fluid and dilution fluid. The receptacle 184 is open to the atmosphere, and has a nipple 181 for supplying sheath fluid, and a nipple 182 for discharging sheath fluid, each having the same height, and a nipple 183 is provided on the bottom part for discharging sheath fluid and dilution fluid.

Optical System and Fluid System

Figure 16:
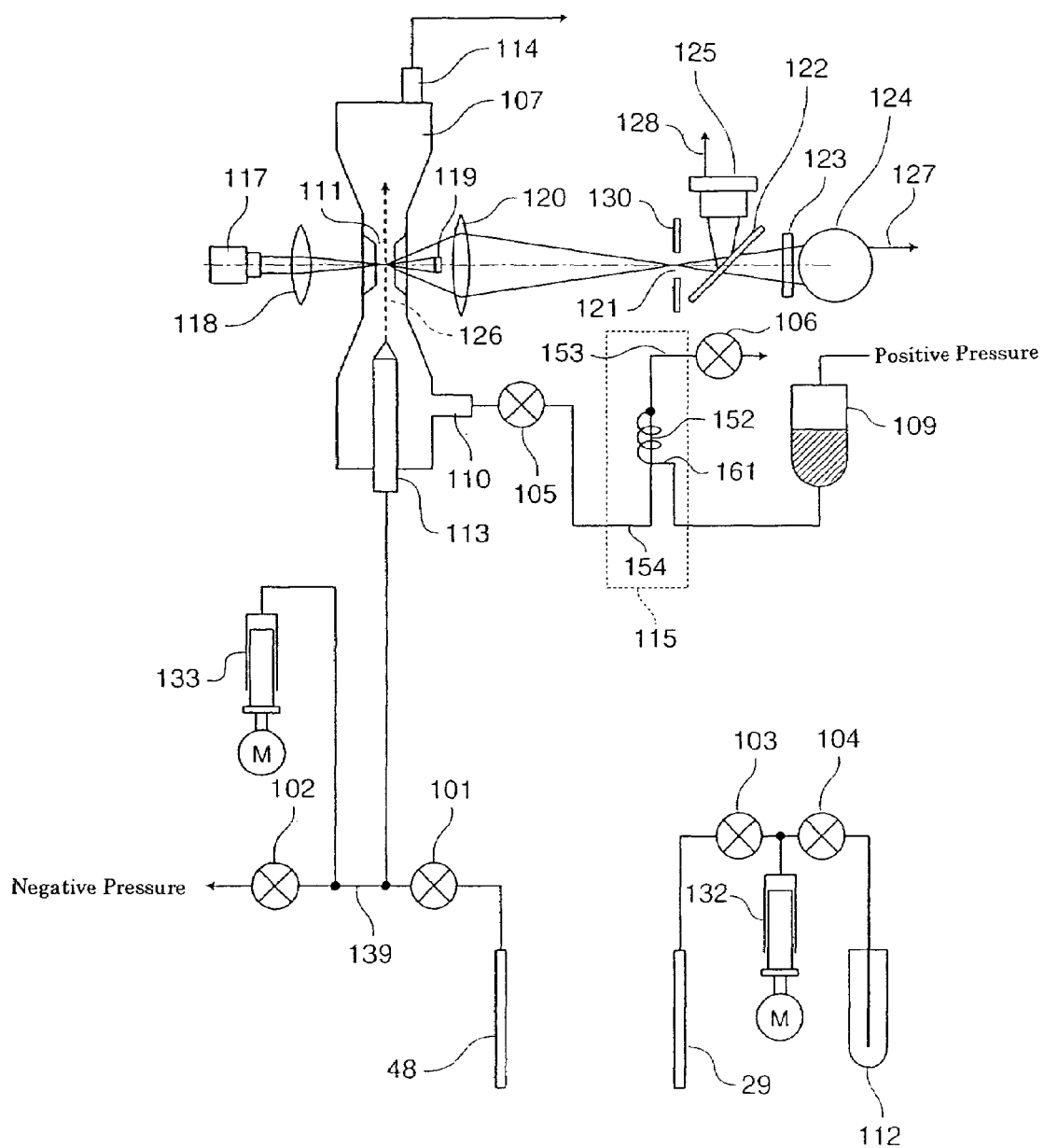
FIG. 16 illustrates parts of the optical system and fluid system of a sample analyzer embodying features of the present invention.
Figure 17:
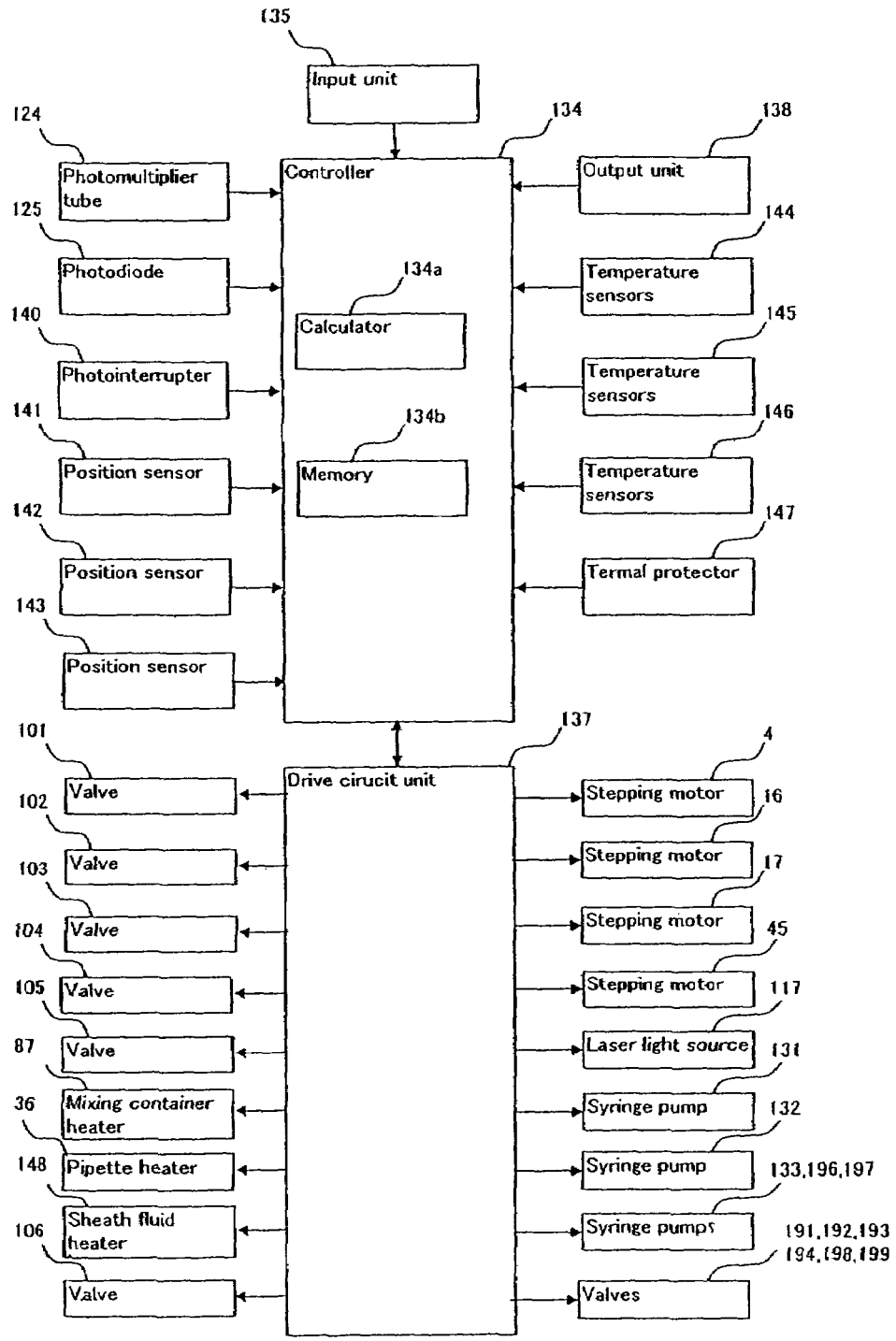
FIG. 17 shows a block diagram showing the control system of a sample analyzer embodying features of the present invention.

FIG. 16 illustrates parts of the optical system and fluid system of a sample analyzer using the sample preparation device shown in FIG. 1. FIG. 17 shows a block diagram of the control system of the sample analyzer.

As shown in FIG. 16, a sheath flow cell 107 is provided with a nozzle 113 for discharging an analysis sample upward toward an orifice 111, sheath fluid supply port 110, and drainage port 114. Near the sheath flow cell 107 are provided a laser light source 117, condenser lens 118, beam stopper 119, collector lens 120, light shield 130 with a pinhole 121, dichroic mirror 122, filter 123, photomultiplier tube 124, and photodiode 125. Thus, a flow cytometer is shown in part of FIG. 16.

A sheath fluid container 109 under positive pressure is connected to the sheath fluid supply port 110 through a temperature control unit 115 and a valve 105. The drainage port 114 is connected to a discard chamber (not shown). The third pipette 48 of the sample preparation device (FIG. 1) is connected to the nozzle 113 through a valve 101. A negative pressure source is connected through the flow path 139 and a valve 102. A syringe pump 133 is connected on the valve 102 side of the flow path 139. The temperature control unit 115 is connected to a discard chamber (not shown) through a valve 106, so as to appropriately remove air bubbles accumulating inside.

The second pipette 29 of the sample preparation device (FIG. 1) is connected to the syringe pump 132 through a valve 103. The syringe pump 132 is connected to a stain container 112 through a valve 104.

Figure 26:
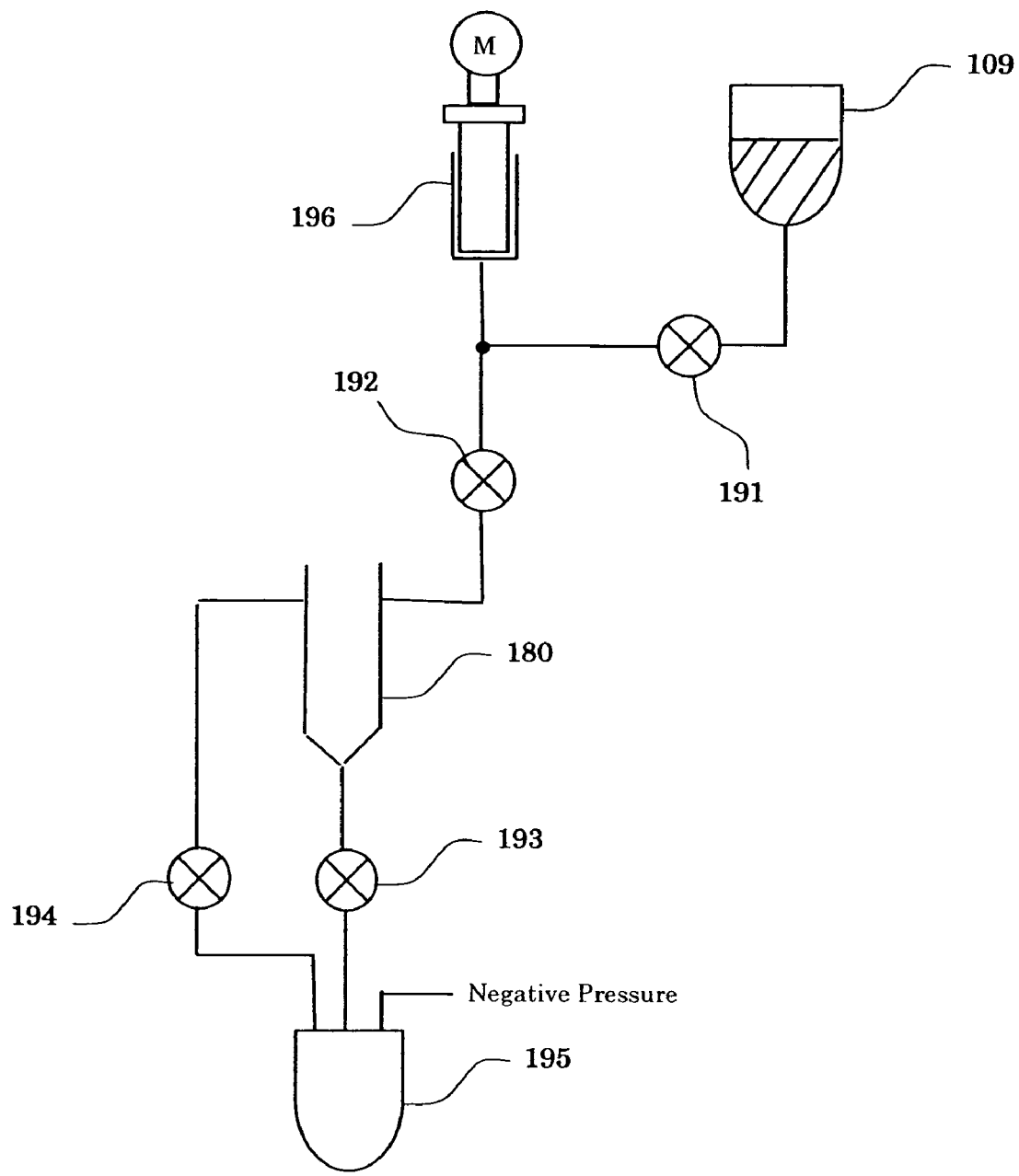
FIG. 26 shows part of the fluid system of a sample analyzer embodying features of the present invention.

As shown in FIG. 26, the washing chamber 180 is connected to a syringe pump 196 through a valve 192. The valve 192 is connected to the sheath container 109 through a valve 191. The washing chamber 180 is connected to a drainage chamber 195 for accommodating used sheath fluid, dilution solution, and the like through a valve 194 and valve 193.

Figure 27:
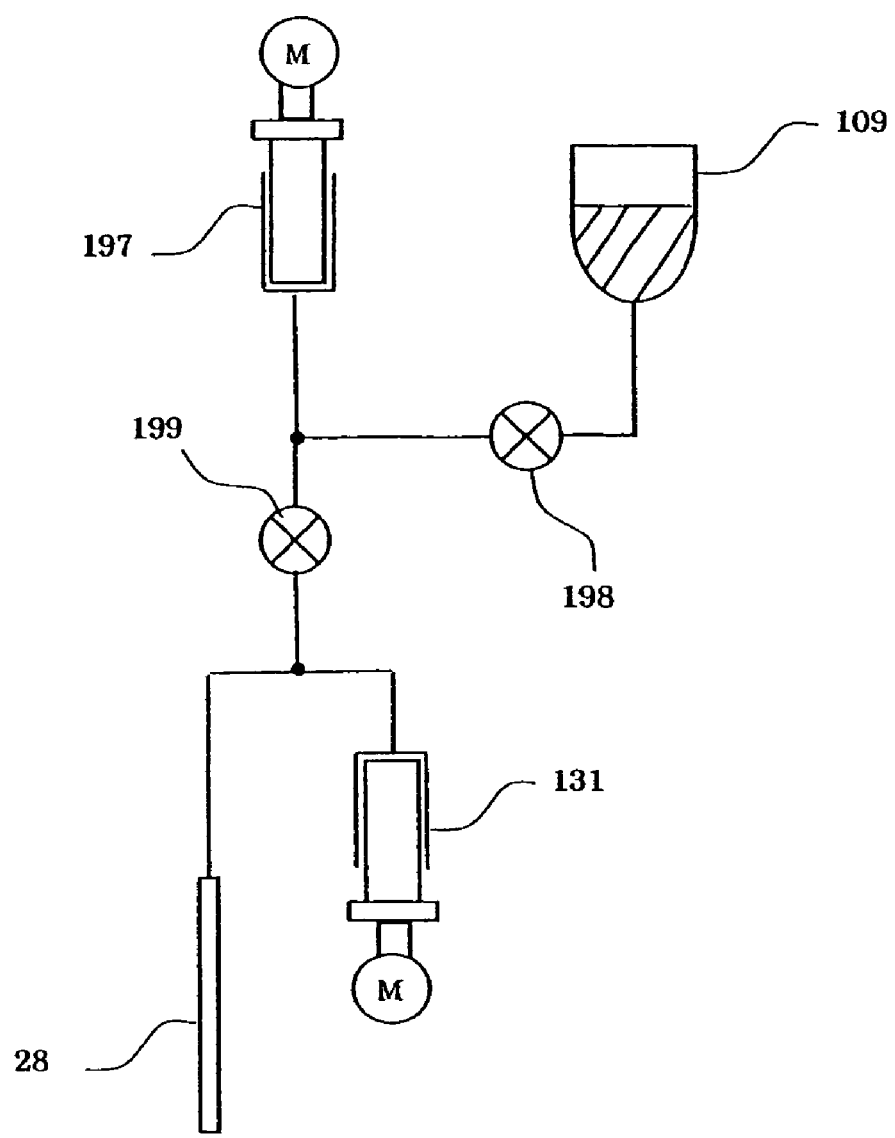
FIG. 27 shows part of the fluid system of a sample analyzer embodying features of the present invention.

As shown in FIG. 27, the first pipette 28 is connected to a syringe pump 131, and is further connected to a syringe pump 197 through a valve 199. The valve 199 is connected to the sheath fluid container 109 through a valve 198.

Temperature Control Unit

Figure 20:
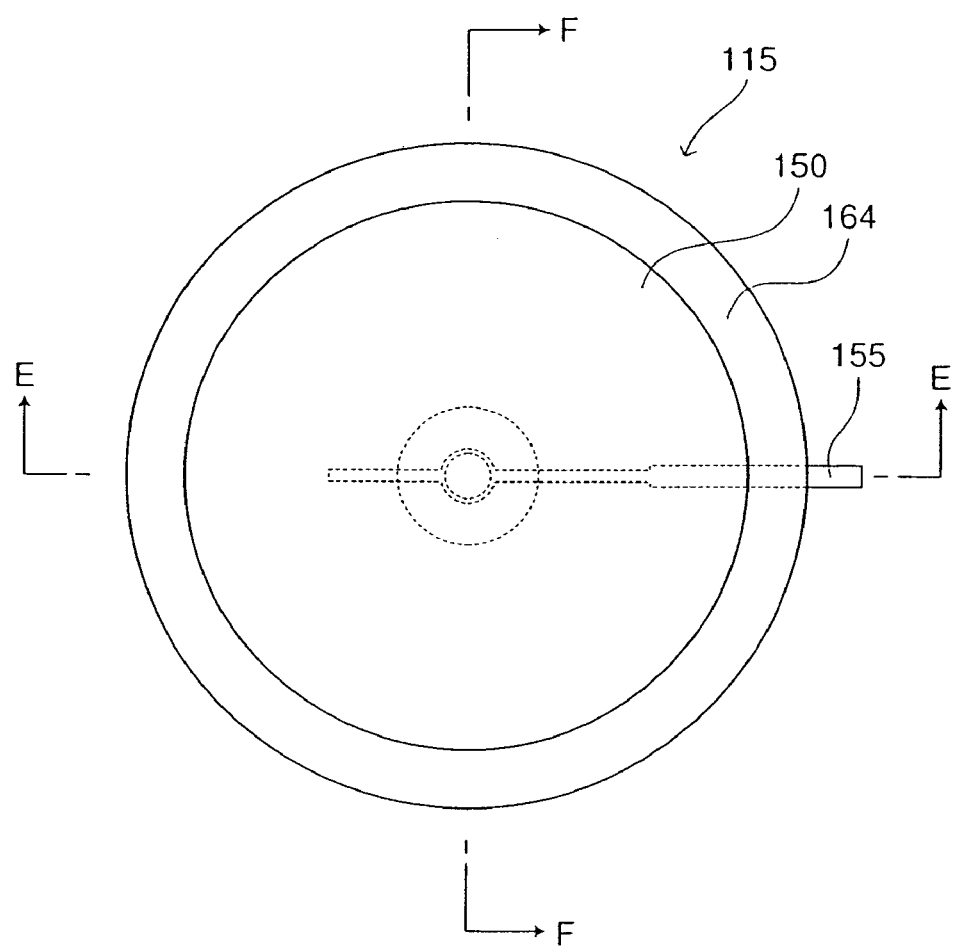
FIG. 20 shows a top view of a temperature control unit of an embodiment of the present invention.
Figure 21:
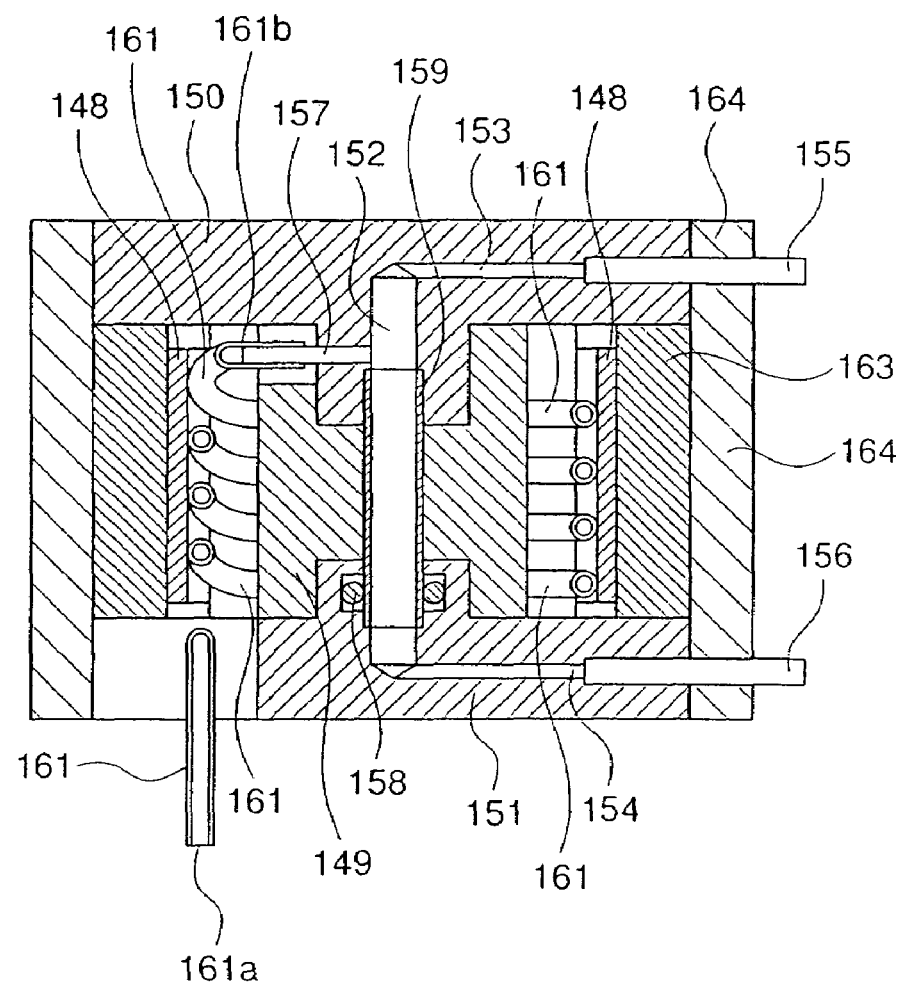
FIG. 21 shows a cross-sectional view along the line E-E of FIG. 20.
Figure 22:
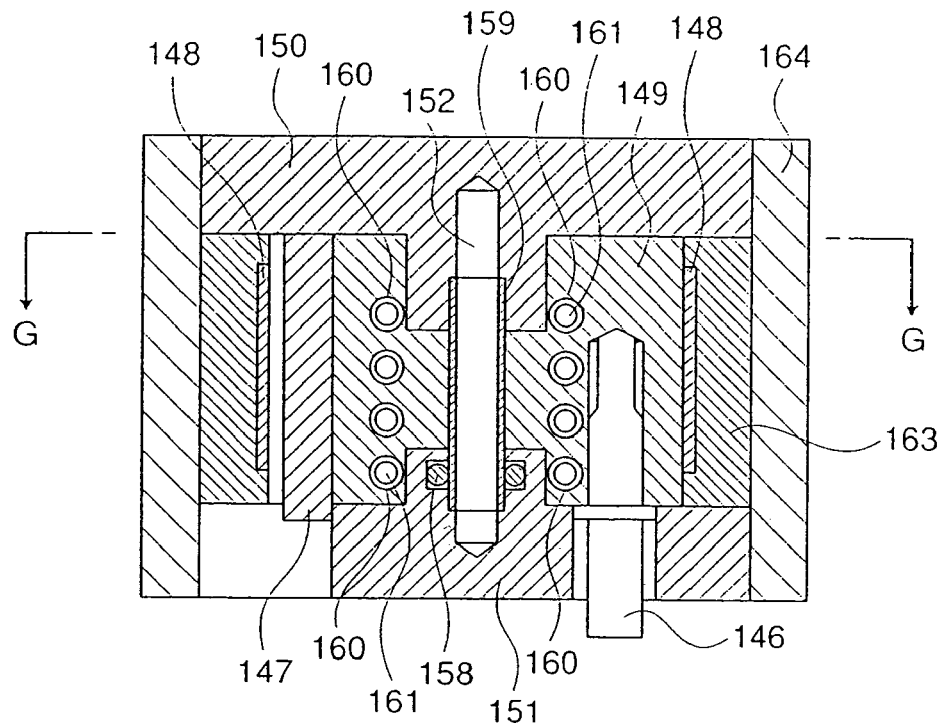
FIG. 22 shows a cross-sectional view along the line F-F of FIG. 20.
Figure 23:
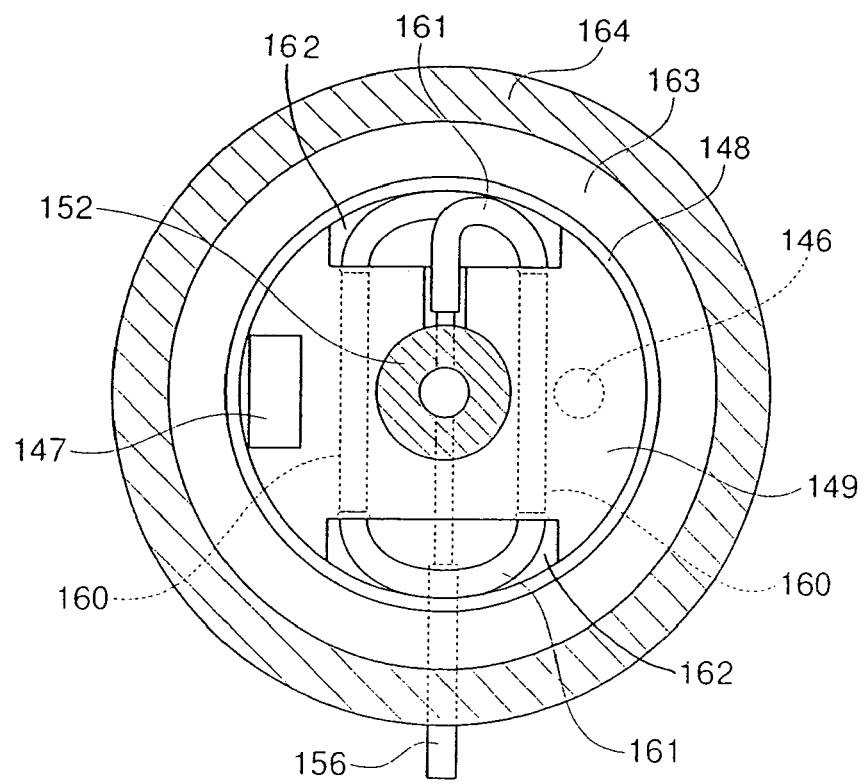
FIG. 23 shows a cross-sectional view along the line G-G of FIG. 20.

FIG. 20 shows a top view of the temperature control unit 115. FIG. 21 shows a cross-sectional view along the line E-E in FIG. 20. FIG. 22 shows a cross-sectional view along the line F-F in FIG. 20. FIG. 23 shows a cross-sectional view along the line G-G in FIG. 22.

As shown in FIG. 21, a metal heat accumulator block 149 (formed of brass) is provided at the center of the temperature control unit 115, and disk-like heat insulator blocks 150 and 1051 (formed of polyacetal resin) are respectively fitted on the top and bottom surfaces of the metal block 149. An air bubble elimination flow path 152 (internal diameter 3.2 mm) is formed in a perpendicular direction from the heat insulator blocks 150 to 151 at the center of the metal block 149.

The interiors of the heat insulator blocks 150 and 151 are provided, respectively, with first and second drainage paths 153 and 154 (internal diameter 1 mm) in a horizontal direction. One end of the first drainage path 153 is connected to the top end of the air bubble elimination path 152, and the other end is connected to a an external tube connector nipple 155 (internal diameter 1.5 mm, formed of stainless steel) protruding in a horizontal direction from the heat insulating block 150.

One end of the second drainage path 154 is connected to the bottom end of the air bubble elimination path 152, and the other end is connected to an external tube connector nipple 156 (internal diameter 1.5 mm, formed of stainless steel) protruding in a horizontal direction from the heat insulating block 151.

Furthermore, the heat insulating block 150 is provided with a supply path horizontally connected between the top end and bottom end of the air bubble elimination path 152, and a nipple 157 (internal diameter 0.9 mm) is inserted into the supply path.

A pipe 159 (stainless steel) is installed in the interior wall of the air bubble elimination path 152. The top end of this pipe 159 is press-fitted into the heat insulating block 150, and the bottom end is inserted into the heat insulating block 151 through an O-ring 158 so as to be watertight. In this way, the fluid flowing through the air bubble elimination path 152 is prevented from contacting the metal block 149.

As shown in FIGS. 22 and 23, the metal block 149 is provided with a total of eight through-holes 160 provided in parallel rows of four so as to be symmetrical on the bilateral sides of the air bubble elimination path 152. One supply tube 161 (internal diameter 0.8 mm, formed of FEP) passes through sequentially from the bottom through-hole 160 to the top through-hole 160, so as to spiral around the air bubble elimination path 152.

As shown in FIG. 21, the bottom end 161a of the supply tube 161 extends downward from the heat insulating block 151, and the top end 161b is connected to the nipple 157. As shown in FIG. 23, a concavity 162 is formed in the metal block 149 at the bilateral ends of the through-hole 160, and the bent part of the supply tube 161 extending in a spiral shape is accommodated within the concavity 162.

A plate-like sheath fluid heater 148 is provided so as to cover the side surface of the metal block 149. As shown in FIGS. 21 and 22, a heat shield 163 (formed of foamed polyethylene) is provided between the heat insulating blocks 150 and 151 so as to cover the sheath fluid heater 148.

Furthermore, a heat shield 164 (formed of foamed polyethylene) is provided so as to cover the heat shield 163 and the side surfaces of the insulating blocks 150 and 151. A temperature sensor (thermistor) 146 and thermal protector (switching element) 147 are provided on the metal block 149, as shown in FIG. 22. In this construction, when sheath fluid is supplied from the bottom end 161a of the supply tube 161 and the nipples 155 and 156 are open, as shown in FIG. 21, the sheath fluid is heated within the supply tube 161 and flows from the nipples 155 and 156.

When the nipple 155 is closed, the heated sheath fluid not only flows from the nipple 156, but also the air bubbles in the sheath fluid gradually rise up inside the air bubble elimination path 152 and accumulate at the top end. That is, since there is a rapid decrease in the flow rate of the sheath fluid flowing from the nipple 156 to the air bubble elimination path 152, the air bubbles rise and are eliminated upward when the fluid in the air bubble elimination path 152 falls.

By closing the nipple 156 and opening the nipple 155 and supplying sheath fluid from the supply tube 165 as necessary, the air bubbles accumulated near the top end of the air bubble elimination path 152 are eliminated together with the sheath fluid draining from the nipple 155.

The temperature of the metal block 149 is detected by the temperature sensor 146, and the sheath fluid heater 148 heats the metal block 149 so as to maintain a temperature of 42° C. When the metal block 149 becomes overheated, the thermal protector 147 operates so as to block the current to the sheath fluid heater 148.

First Pipette

Figure 24:
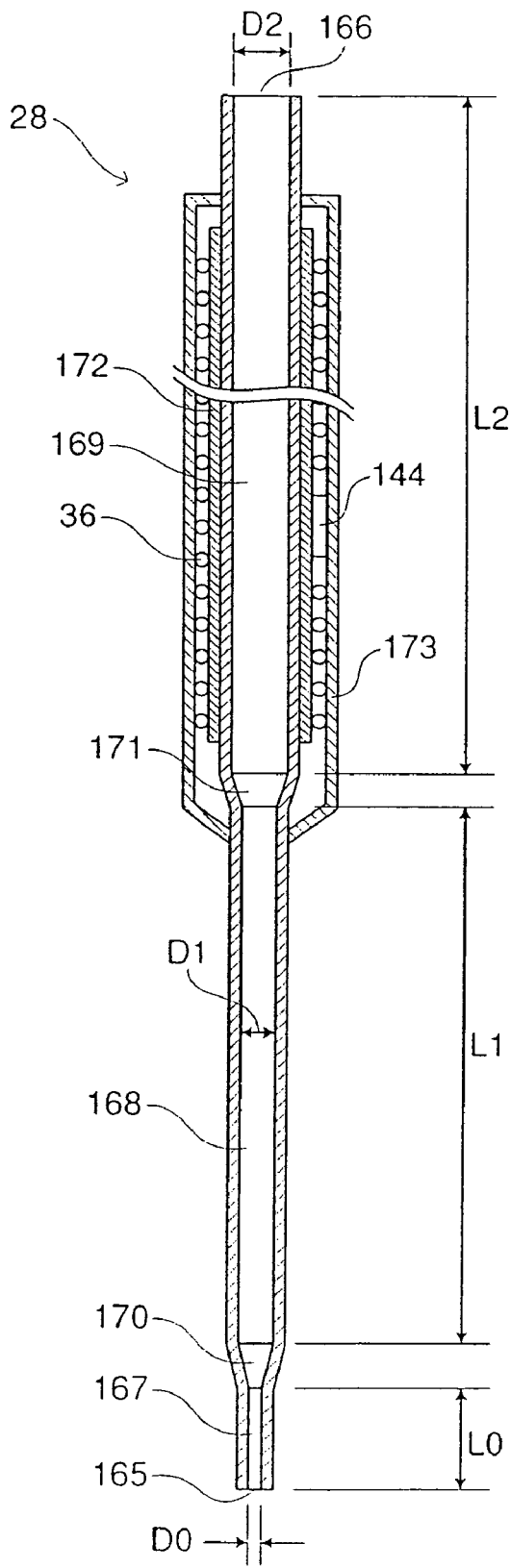
FIG. 24 shows a longitudinal view of the pipette in an embodiment of the present invention.

FIG. 24 shows a longitudinal sectional view of the first pipette 28. As shown in the drawing, the first pipette 28 is formed of stainless steel and has a slender and hollow barrel shape extending from the tip 165 to the base 166. The first pipette 28 has, sequentially, from the tip 165 to the base 166, a suction part 167 with a length L0 and an internal diameter D0, a sample part 168 with a length L1 and an internal diameter D1, and a reagent part 169 with a length L2 and an internal diameter D2.

D0, D1, and D2 are related as D0<D1<D2. In the present embodiment, D0=0.6 mm, D1=1.5 mm, and D2=2.1 mm; and L0=3 mm, L1=45 mm, and L2=150 mm. Accordingly, the volumes of the sample part 168 and the reagent part 169 are 79.5μ and 520μ, respectively.

The suction part 167 is narrow to suction sample and reagent without excess or deficiency. Sample and reagent are accommodated in the sample part 168. Reagent alone is accommodated in the reagent part 169, and no sample is accommodated therein.

The suction part 169 and sample part 168, and the sample part 168 and reagent part 169 are connected, respectively, by connectors 170 and 171, which have tapered orifices. The reagent part 169 is provided with a heat accumulator pipe 172 formed of copper on its outer wall, and the outer wall of the heat accumulator pipe 172 is provided with a pipette heater 36.

The pipette heater 36 is formed of covered Nichrome wire, and is coiled around the outer wall of the heat accumulator pipe 172. A temperature sensor (thermistor) 144 is provided on part of the outer wall of the heat accumulator pipe 172. The reagent part 169 is provided with a protective cover 173 formed of stainless steel for covering the pipette heater 36 and the temperature sensor 144.

Control System

As shown in FIG. 17, a controller 134 is provided with a calculator 134a and a memory 134b. The controller receives the output from an input unit 135, photomultiplier tube 124, and photodiode 125, and outputs analysis conditions and analysis results to an output unit 138. A microcomputer, personal computer or the like including a CPU, ROM, RAM and the like may be used as the controller 134.

The photointerrupter 140 detects the initial position of the turntable 42 as described above, and the position sensors 141 through 143 detect horizontal position of the horizontally movable plate 8, and the vertical positions of the first pipette 28, second pipette 29, and the catcher 27.

The temperature sensors 144 through 146 are sensors (thermistors) which respectively detect the temperature of the first pipette 28, second holder 86, and the temperature control unit 115. The thermal protector 147 is a switching element which prevents overheating of the temperature control unit 115 as described above.

The controller 134 receives the output from the photointerrupter 140, position sensors 141 through 143, temperature sensors 144 through 146, and thermal protector 147, and controls the drive circuit unit 137. In this instance, the controller 134 is a microcomputer, and the input unit 135 and the output unit 138 are integratedly formed touch panel type LCDs.

The drive circuit unit 137 is provided with a stepping motor drive circuit, syringe pump drive circuit, valve drive circuit, heater drive circuit, and laser drive circuit. The drive circuit 137 receives the output from the controller 134, and drives the stepping motors 4, 16, 17, and 45 shown in FIG. 1, syringe pumps 131 through 133 shown in FIG. 16, and syringe pumps 196 and 197, valves 101 through 106, 191 through 194, 198 and 199, heaters 36, 87, 148, and laser light source 117, as shown in FIG. 16.

Dilution Solution Composition

The composition of the dilution solution accommodated in the dilution solution container 34 is described below.

| | |
|---|---|
| Citric acid | 100 mmol |
| Sodium sulfate | 90 mmol |
| Amidosulfuric acid | 100 mmol |
| NaOH | Amount to obtain a solution pH of 2.5 |
| Tetradecyltrimethylammonium salt | 1 g |
| Purified water | 1 liter |

This dilution solution has a pH of 2.5. Since the dilution solution is acidic, the cell membrane and cell walls of the bacteria in the urine are damaged. Accordingly, the bacteria in the samples can be reliably stained with staining solution, and can be reliably detected by the flow cytometer shown in FIG. 16. When this dilution solution is used as a washing solution, since it is acidic, it damages the cellular membrane and cellular walls of the bacteria in the urine so as to weaken the adhesion of the bacteria to the pipette and provides highly effective washing. Polymethylene colorant may be used as a staining solution. A representative staining solution is described in detail in United States Patent Application Publication No. 2002/0076743.

Sheath Fluid Composition

The composition of the sheath fluid used in the sample analyzer of the present embodiment is described below.

| | |
|---|---|
| Sodium chloride | 53.0 g |
| Maleic acid | 0.5 g |
| Tris(hydroxymethyl)amino methane | 1.51 g |
| EDTA-2K | 0.2 g |
| Purified water | 1.0 liter |

This sheath fluid has a pH of 7.8.

Analysis Sample Preparation Operation

The analysis sample preparation operation is described below.

(A) Turntable Initialization

Figure 19:
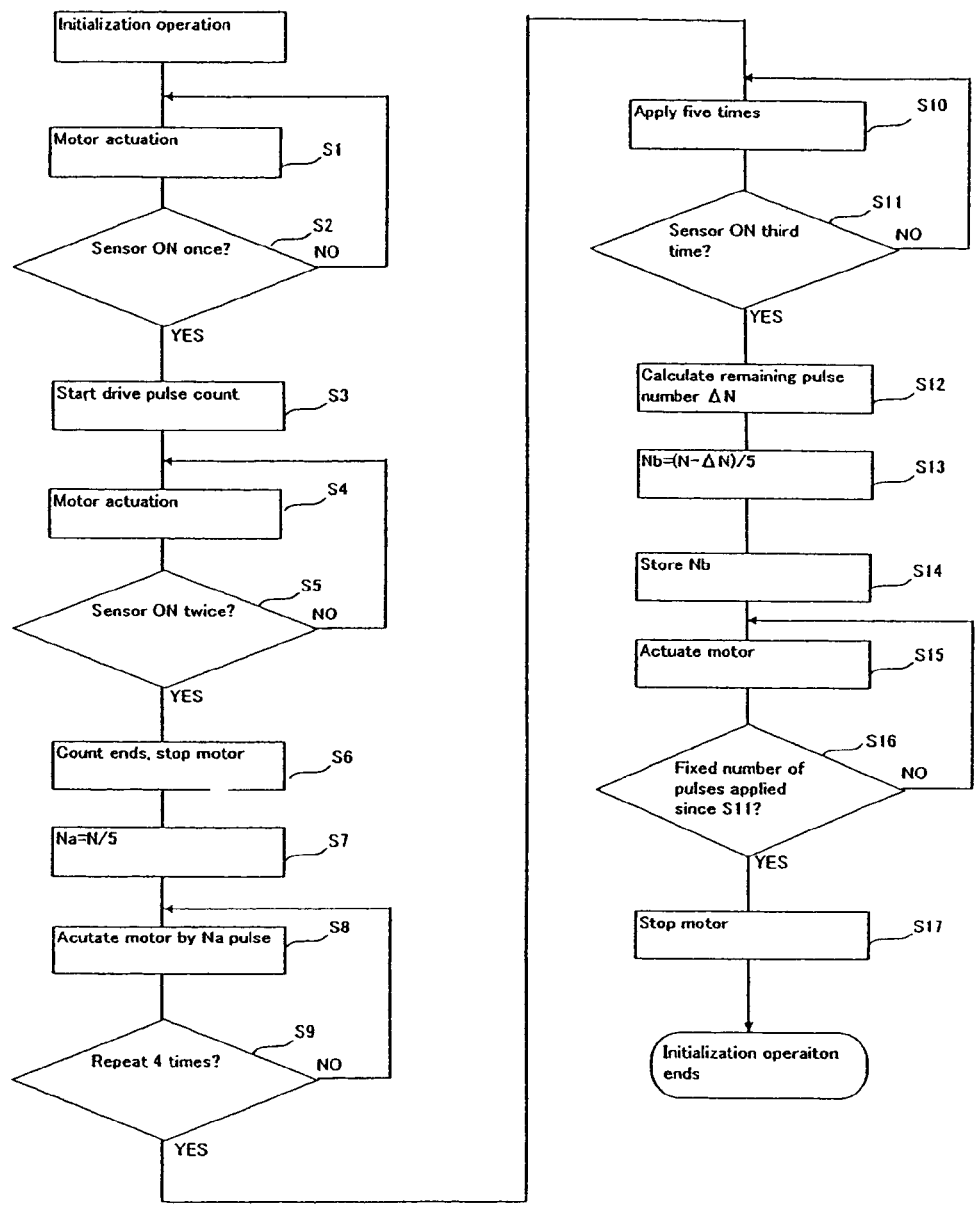
FIG. 19 shows a flow chart for the initialization operation of the turntable of an embodiment of the present invention.

First, the initialization operation is described wherein a required drive pulse number Nb is determined for the stepping motor 45 to rotate the sample container Ts only one pitch on the turntable 42 based on the flow chart of FIG. 19.

When the power source of the control system shown in FIG. 17 is turned ON, a drive pulse is supplied to the stepping motor 45, and the turntable 42 is rotated in the clockwise direction (S1). Then, the light shield 62a shields the photo-interrupter 140 (hereinafter referred to as "sensor ON") (S2), the count of the drive pulse applied to the stepping motor 45 starts (S3), and the motor actuation continues (S4). When the sensor is turned ON (S5), the application of the drive pulse to the stepping motor 45 is stopped, the count ends for the drive pulse number N required for one rotation of the turntable 42, and the stepping motor 45 stops (S6).

The number of drive pulses required to rotate the turntable 42 one pitch is calculated as Na=N/5 (S7). Na is a value which ignores over rotation due to inertia.

Next, Na individual drive pulses are repeatedly applied to the stepping motor 45, and the turntable 42 is repeatedly rotated and stopped (S8, S9, and S10).

This time, since the turntable 42 rotates with an accumulation of over rotations due to inertia each time the turntable stops, the sensor is turned ON while the fifth Na individual drive pulses are being applied insofar as the Na individual drive pulses have not all been applied (S11), and the number of drive pulses remaining is only ΔN. Then, the remaining number of pulses ΔN is calculated as the accumulated amount of over rotation (S12).

The Na calculated in S7 is corrected as Nb=(N−ΔN)/5 in consideration of the amount of over rotation (S13), and stored in the memory 134b (FIG. 17) as the correct drive pulse number to rotate the turntable 42 one pitch (S14).

A predetermined number of drive pulses are applied to the stepping motor 45 after the sensor is turned on in S11, and when the turntable 42 reaches a position that is most convenient for a user to remove the container holder 61 from the rotating plate 62, that is, a position at which the guide block 63 crosses the straight line L at a right angle in FIG. 2, the stepping motor stops, and the turntable initialization operation ends (S15, S16, and S17).

(B) Specimen Container and Mixing Container Placements

Next, the handle 71 shown in FIG. 6 is grasped and pulled toward the front so as to slide the container holder 61 to the front on the rotating plate 62, and the container holder 61 is then removed from the rotating plate 62. A user then loads sample containers Ts containing different 300 μL samples (e.g., urine) into the five holes 74 of the first holders 68 of the container holder 61 shown in FIG. 9, and loads the empty mixing containers Tm into the five empty container holes 67.

Then, the user grasps the handle 71 and installs the container holder 61 on the rotating plate 62 as shown in FIG. 8. At this time, the container holder 61 slides onto the rotating plate 62 so as to insert the guide block 63 shown in FIG. 8 into the channel 70 shown in FIG. 11, and the positioning pin 65 is inserted into the positioning hole 69 via the force exerted by the compression spring 64 as shown in FIG. 6. Accordingly, the container holder 61 is stopped by the protrusion 66 so as to position the container holder 61 on the same axis as the rotating plate 62.

(C) Automated Preparation Operation

The processes (1) through (26) are automatedly executed by the control system shown in FIG. 17.

(1) When a user places the container holder 61 on the rotating plate 62 as described above and a start command is input to the input unit 135 (FIG. 17), the stepping motor 45 rotates in a clockwise direction so as to cause the turntable 42 to be rotated in conjunction therewith, and when the sensor is turned ON, the turntable 42 is stopped at the initial position shown in FIG. 2. This time, the first sample container Ts and the two mixing containers Tm on both sides of the sample container Ts are aligned on the straight line L. At the same time, the first holder 68, which accommodates the first sample container Ts, confronts the magnet coupling 91 as shown in FIG. 5.

(2) Then, the stepping motors 4 and 17 shown in FIG. 1 are operated, the mixing container Tm on the right side, among the two mixing containers Tm on the straight line L shown in FIG. 2, is held by the catcher 27 and inserted into the second holder 86 of the mixing container rotation mechanism 44. At this time, a current is already flowing to the film heater 87 (FIG. 4) of the mixing container rotation mechanism 44 and the temperature of the second holder 86 is maintained at 42° C.

(3) Next, the stepping motors 4 and 17 are operated, and the empty mixing container Tm remains in the second holder 86, and the catcher 27 is pulled from the second holder 86.

(4) Then, the valve 198 (FIG. 27) is opened, and after the syringe pump 197 performs a suctioning operation, the valve 198 is closed and the valve 199 is opened and the syringe pump 197 performs a discharge operation so as to fill the sample part 168 of the first pipette 28 and the reagent part 169 (FIG. 24) and the flow path connecting the two with sheath fluid.

(5) Thereafter, the stepping motors 4 and 16 are actuated, and the first pipette 28 is inserted into the dilution solution container 34 and 340 μL of the dilution solution is suctioned to the reagent part 169 (FIG. 24), and heated to 42° C. by the pipette heater 36.

(6) Next, the stepping motor 16 is actuated and the first pipette 28 is withdrawn from the dilution solution container 34, and 20 μL of air is suctioned into the sample part 168. In this way an air gap having a 20 μL volume is formed.

(7) Then, the stepping motors 4 and 16 are actuated, and the first pipette 28 is inserted into the sample container Ts located on the straight line L in FIG. 2. At this time, the first pipette 28 is held at a position which is eccentric from the axis of the sample container Ts.

(8) Next, the stepping motor 45 rotates in a counter clockwise direction for a predetermined time. In this way the pulley 58 is rotated in a counter clockwise direction, and the sample container Ts on the straight line L is also rotated in a counter clockwise direction. During the rotation of the sample container Ts, the first pipette 28 suctions the sample (40 μL) within the sample container Ts and discharges the sample into the sample part 168 (FIG. 24). Then, the suctioning and discharging operations are repeated. The sample is thoroughly mixed by the rotation of the sample container Ts relative to the eccentrically positioned first pipette 28, and the suctioning and discharging operation performed by the first pipette 28.

(9) After the first pipette 28 has discharged all of the sample of the sample part 168, 50 μL of the sample is suctioned from the sample container Ts. In the sample part 168, an air gap having a 20 μL volume is formed between the suctioned sample and the dilution solution via the previously described process (6), and the sample and the dilution solution are not mixed.

(10) Next, the stepping motors 4 and 16 are actuated, and the first pipette 28 is withdrawn from the sample container Ts and inserted into the empty mixing container Tm held in the second holder 86 as described in process (2). At this time, the first pipette 28 is held at a position which is eccentric to the axis of the held mixing container Tm.

(11) Then, the first pipette 28 discharges the 340 μL of solution, which has been heated to 42° C., and the suctioned 50 μL of sample into the mixing container Tm. At the same time, the stepping motor 45 rotates counterclockwise for a predetermined time. Accordingly, the mixing container Tm containing the dilution solution and the sample is rotated about its axis.

During the rotation of the mixing container Tm, the first pipette 28 repeats the suctioning and discharging operation to a maximum volume of approximately 70 μL so that the fluid does not invade the reagent part 169.

A sample uniformly diluted 8 times is prepared by the rotation of the mixing container Tm relative to the eccentrically positioned first pipette 28, and the suctioning and discharging operation performed by the first pipette 28.

(12) Thereafter, the stepping motors 4 and 16 are actuated, and the first pipette 28 is withdrawn from the mixing container Tm.

(13) Then, the stepping motors 4 and 16 are actuated, and the first pipette 28 is inserted into the receptacle 184 of the washing chamber 180.

(14) Next, the valve 199 (FIG. 27) is opened and, via the discharge operation of the syringe pump 197, approximately 2 ml of the sheath fluid filling the first pipette 28 is discharged into the receptacle 184 by the previously described process (4). In this way the inside of the first pipette 28 is washed.

(15) Then, the valve 193 (FIG. 26) is opened, and the sheath fluid discharged into the receptacle 184 is drained into the drainage chamber 195. The valve 193 is then closed.

(16) In parallel with processes (14) and (15), valve 191 is opened, and the syringe pump 196 performs a suctioning operation. The valve 191 is then closed.

(17) Next, the stepping motor 16 is actuated, and the tip of the first pipette 28 is raised to a position approximately 2 cm lower than the nipple 181 and the nipple 182 (FIG. 25).

(18) Then, the valves 192 and 194 (FIG. 26) are opened, and the syringe pump 196 performs a discharge operation. In this way the sheath fluid is injected from the nipple 181 (FIG. 25) into the receptacle 184 and discharged from the nipple 182, and the outside of the first pipette 28 is washed by the flow of the sheath fluid generated at this time. The valves 192 and 194 are then closed.

(19) Next, the valve 193 is opened, and the sheath fluid inside the receptacle 184 is drained into the drainage chamber 195. The valve 193 is then closed.

(20) Then, the stepping motors 4 and 17 are actuated, and the second pipette 29 is inserted into the mixing container Tm. At this time the second pipette 29 is held at a position which is eccentric to the axis of the mixing container Tm.

(21) Then, the second pipette 29 discharges 10 μL of a staining solution supplied from the stain container 112 shown in FIG. 16 into the mixing container Tm. At the same time, the stepping motor 45 rotates in a counter clockwise direction for a predetermined time. Accordingly, the mixing container Tm is rotated about its axis. During the rotation of the mixing container Tm, the second pipette 29 repeats the suctioning and discharging operations. The staining fluid is uniformly mixed with the dilute sample by the rotation of the mixing container Tm relative to the eccentrically positioned second pipette 29, and the suctioning and discharging operation performed by the second pipette 29 so as to prepare an analysis sample. The prepared analysis sample is held at 42° C. by the film heater 87 of the mixing container rotation mechanism 44.

(22) Thereafter, the stepping motors 4 and 17 are actuated, and the second pipette 29 is withdrawn from the mixing container Tm.

(23) Then, the stepping motors 4 and 17 are actuated, the second holder 86 is withdrawn from the mixing container Tm by the catcher 27, and transported to the third pipette 48, whereupon the third pipette 48 is inserted into the mixing container Tm. Then, the third pipette 48 suctions analysis sample from the mixing container Tm.

(24) Next, the stepping motors 4 and 17 are actuated, and the catcher inserts the empty mixing container Tm into a discard hole 35 of the container discard unit 46 where it is discarded.

(25) Then, the stepping motors 4 and 17 are actuated, and the catcher grips and lifts the top part of the washing unit 52, and inserts the third pipette 48 into the washing unit 52. In this way the third pipette 48 is washed.

(26) Then, the stepping motors 4, 16, and 17 are actuated, and the washing unit 52 is returned to the position shown in FIG. 1, and the first pipette 28, second pipette 29, catcher 27, and the horizontally movable plate 8 are returned to the positions shown in FIG. 1.

Next, when Nb individual drive pulses are applied to the stepping motor 45 and the turntable 42 is rotated in a clockwise direction, the next sample container Ts and empty mixing containers Tm are aligned on the straight line L of FIG. 2 so as to prepare the next analysis sample.

Sample Analysis Operation

In the structure shown in FIGS. 16 and 17, when the valves 101 and 102 are opened during a prescribed time, the analysis sample prepared by the sample preparation unit shown in FIG. 1 and maintained at a temperature of 42 C flows into the flow path 139 between the valves 101 and 102 through the third pipette 48 via the negative pressure. Thereafter, the valves 101 and 102 are closed.

Next, the sample is discharged from the nozzle 113 to the sheath flow cell 107 when the syringe pump 133 pushes a fixed amount of the sample in the flow path 139 to the nozzle 113.

At the same time, sheath fluid heated to 42° C. by the temperature control unit 115 is supplied to the sheath flow cell 107 by opening the valve 105.

In this way the sample is encapsulated in sheath fluid, and a sheath flow is formed which is narrowed by the orifice 111. The one side of the orifice 111 has a rectangular slot measuring 100 to 300 μm and formed of optical glass.

Particles or tangible components included in the sample can flow one by one in a row through the orifice 111 by forming the sheath flow in this way. The sample and sheath fluid which have passed through the orifice 111 are discharged from the discharge port 114.

Then, laser light emitted from a laser light source 117 is condensed to an oval by a condenser lens 118 and directed at the sample flow 126 flowing through the orifice 111. The size of this oval is approximately the same as the diameter of analysis particles in the direction of the sample flow, for example, about 10 μm, and is sufficiently larger than the analysis particle diameters in a direction perpendicular to the sample flow direction, for example, approximately 100 to 400 μm.

The laser light which has passed through the flow cell 107 without impinging the particles contained in the sample is blocked by the beam stopper 119. Forward scattered light and forward fluorescent light from the particles irradiated by the laser light are collected by the collector lens 120, pass through the pinhole 121 of the light shield 130, and reach the dichroic mirror 122.

The long wavelength scattered fluorescent light directly passes through the dichroic mirror 122 and is detected by a photomultiplier tube 124 after scattered light is eliminated by the filter 123, and is then output as a fluorescent signal 127 (pulse-like analog signal).

The scattered light is reflected by the dichroic mirror 122, received by the photodiode 125, and output as a scattered light signal 128 (pulse-like analog signal). Then, the fluorescent light signal 127 and the scattered light signal 128 are input to the controller 134 shown in FIG. 17.

The calculator 134a calculates the scattered light pulse width Fscw and the scattered light intensity Fsc from the maximum value and pulse width of the scattered light signals 128.

The calculator 134a similarly calculates the fluorescent light pulse Flw and fluorescent light intensity Fl from the pulse-like fluorescent light signal 127.

The controller 134 creates distribution maps (histogram and scattergram) based on the obtained Fscw, Fsc, Flw, and Fl, and classifies leukocytes and bacteria. Then, the classified particles are counted and converted to a number per 1 μL of sample. The result is output to the output unit 138 together with each type of distribution map. This completes the analysis operation of a single analysis sample. The samples of the four remaining sample containers Ts are similarly subjected to the sequential rotation of the turntable 42, analysis sample preparation, and analysis operation.

Washing Operation

When the particle count result indicates the presence of a bacteria population of $10^7$ per 1 μL of sample or greater, the washing operation performed in the automated preparation process (14) and the like does not produce adequate washing of the first pipette 28 (particularly the inside of the first pipette 28), and this may adversely affect the measurement result of the subsequent analysis sample. Therefore, in this instance, the washing operation described below is performed. A threshold setting unit (not shown) may be provided in the controller 134 so as to enable the user of the apparatus to set a value (threshold) of $10^7$.

(1) The stepping motors 4 and 16 are actuated, and the first pipette 28 is inserted in the dilution solution container 34, and 340 μL of dilution solution is suctioned to the reagent part 169 (FIG. 24).

(2) Next, the stepping motors 4 and 16 are actuated, and the first pipette 28 is inserted in the receptacle 184 (FIG. 25) of the washing chamber 180. In this process, the dilution solution is kept in the first pipette 28 for approximately 3 seconds.

(3) Then, the syringe pump 131 (FIG. 27) performs a discharge operation and the dilution solution in the reagent part 169 is discharged to the receptacle 184. The syringe pump 131 then performs a suctioning operation and the dilution solution discharged to the receptacle 184 is suctioned into the reagent part 169.

(4) Process (3) is repeated 5 times. Thereafter, the syringe pump 131 performs a discharge operation and the dilution solution in the reagent part 169 is discharged to the receptacle 184. In this way the inside of the first pipette 28 is effectively washed. As mentioned above, the dilution solution is highly effective for washing because it is acidic (pH=2.5) and contains a type of surface-active agent, tetradecyltrimethyl ammonium salt.

(5) Next, the valve 193 (FIG. 26) is opened, and the dilution solution discharged to the receptacle 184 is drained to the drainage chamber 195. The valve 193 is then closed.

(6) In parallel with process (5), the valve 191 is opened, and the syringe pump 196 performs a suctioning operation. The valve 191 is then closed.

(7) Then, the stepping motor 16 is actuated and the tip of the first pipette 28 is raised to a position approximately 2 cm lower than the nipple 181 and the nipple 182 (FIG. 25).

(8) Then, the valves 192 and 194 are opened and the syringe pump 196 performs a discharge operation. In this way the sheath fluid is injected from the nipple 181 (FIG. 25) into the receptacle 184 (FIG. 25) and discharged from the nipple 182, and the outside of the first pipette 28 is washed by the flow of the sheath fluid generated at this time. The valves 192 and 194 are then closed.

(9) Next, the valve 193 is opened and the sheath fluid inside the receptacle 184 is drained into the drainage chamber 195. The valve 193 is then closed.

The syringe pump 132 and valves 103 and 104 shown in FIG. 16 operate during the above-described analysis sample preparation process (21). That is, the valve 104 is opened, and a staining solution is once suctioned from the stain container 112 by the syringe pump 132, the valve 104 is then closed and the valve 103 is opened, and a predetermined amount of the suctioned staining solution is discharged from the second pipette 29 by the syringe pump 132. Furthermore, the valve 103 is then closed, and the syringe pump 132 operates reciprocally so as to perform the suction and discharge operations to the second pipette 29.

This sample analyzer improves the washing capability without reducing the processing capability of the apparatus, without increasing the amount of washing solution used, and without enlarging the apparatus.

Although the embodiment described above is constructed so that a sample suctioned from a sample container held by a first holder 68 is discharged into a mixing container held by a second holder 86, the present invention is not limited to this arrangement, inasmuch as various structures may be used, such as suctioning a sample from a sample container positioned at another location and discharging this sample to a mixing container held by the first holder 68 and the like.

Sample suctioned from the pipette of the sample analyzer of the present embodiment may be fluids such as urine, peritoneal fluid, pleural fluid, bone marrow fluid, bile, blood, and the like from lactating animals including humans, and also beverages, organic and inorganic foods, and the like.

In addition to the optical detection units such as a flow cytometer and the like, electrical property detection units such as electrical resistance sensors and the like used for erythrocyte sensors in hematocytometers also may be used as the detection unit.

It is desirable that the dilution solution used in the sample analyzer of the present invention has a pH less than about 5.0. A pH of between about 2 and about 3 is particularly desirable.

Furthermore, the dilution solution used in the sample analyzer of the present invention may include an acidic buffering agent.

The acidic buffering agent is not specifically limited, and suitable examples include but are not limited to citric acid, phthalic acid, glycine, succinic acid, lactic acid, β-alanine, ε-aminocapronic acid, and fumaric acid, and the like, and combinations thereof.

The dilution solution used in the sample analyzer of the present invention may include a surface-active agent.

Examples of useful surface-active agents include but are not limited to cationic surface-active agents, anionic surface-active agents, ampholytic surface-active agents, nonionic surface-active agents, and the like, and combinations thereof.

Although cationic surface-active agents are not specifically limited, quaternary ammonium salts having the structural formula shown below are desirable:

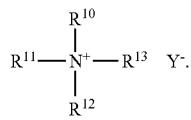

In the formula, R14 represents an alkyl group having 6 to 18 carbon atoms or $(C_6H_5)$—$CH_2$—; R11, R12 and R13 represent the same or different alkyl groups or benzyl groups having 1 to 3 carbon atoms; and Y represents a halogen ion.

Examples of useful alkyl groups with 1 to 3 carbon atoms include methyl, ethyl, propyl, and the like. Examples of useful alkyl groups with 6 to 18 carbon atoms include but are not limited to hexyl, heptyl, octyl, decyl, dodecyl, tetradecyl, and the like. Examples of useful halogens include flourine, bromine, iodine, chlorine, and the like. Specifically, suitable materials are hexyltrimethyl ammonium salt, octyltrimethyl ammonium salt, decyltrimethyl ammonium salt, dodecyltrimethyl ammonium salt, tetradecyltrimethyl ammonium salt, hexadecyltrimethyl ammonium salt, octadecyltrimethyl ammonium salt, and benzyltrimethyl ammonium salt.

Another example of a cationic surface-active agents are pyridinium salts:

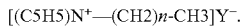

In the formula, n represents 7 to 17; and Y represents a halogen ion. Specifically, suitable materials include octyl pyridinium salt, decyl pyridinium salt, dodecyltrimethyl pyridinium salt, tetradecyltrimethyl pyridinium salt, hexadecyltrimethyl pyridinium salt, and the like. The concentration of the cationic surface-active agent is in a range of about 10 to about 50,000 mg/ml, and is desirably in a range of about 100 to about 3,000 mg/ml.

The anionic surface-active agent is not limited, and suitable useful examples include but are not limited to lauroylsarcosine acid salt as a N-acylaminoacetic acid salt, cocoylsarcosine acid salt, myristoylsarcosine acid salt, oleoylsarcosine acid salt, and the like. Although not limited, the concentration of the anionic surface-active agent may be, for example, in a range of about 0.1 to about 10 mg/ml, and is desirably in a range of about 0.5 to about 5 mg/ml.

The amphoteric surface active agent is not limited, and a useful example is the betaine acetate shown below:

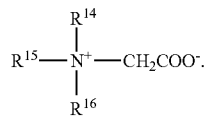

In the formula, R14 represents an alkyl group having 8 to 20 carbon atoms; R15 and R16 represent the same or different alkyl group having 1 to 3 carbon atoms, alkenyl groups or alkynyl groups having 2 to 3 carbons atoms.

The alkyl group with 1 to 3 carbon atoms may be the same as above. Examples of useful alkenyl groups with 2 to 3 carbons atoms include vinyl, allyl, and the like. Examples of useful alkynyl groups with 2 to 3 carbon atoms include acetylenyl, propynyl, and the like. Examples of useful alkyl groups with 8 to 20 carbon atoms include but are not limited to octyl, decyl, dodecyl, tetradecyl, and the like. Representative examples include but are not limited to docecyldimethyl ammonium-betaine acetate, hexadecyldimethyl ammonium-betaine acetate, decyldimethyl ammonium-betaine acetate, and the like. The concentration of the amphoteric surface-active agent may be about 1 to about 100 mg/ml, and a concentration of about 5 to about 20 mg/ml is desirable.

Nonionic surface-active agents are not limited, and suitable examples of polyoxyethylene(n)alkyl ethers have an alkyl group with 10 to 20 carbon atoms, where n represents 10 to 20. Suitable polyoxyethylene(n)alkylphenyl ethers have an alkyl group with 8 to 10 carbon atoms, where n represents 2 to 20, for example, POE (10)octylphenyl ethers, and the like.

Examples of useful surface-active agents other than those described above include but are not limited to triton X-100 (polyethylene-glycol-mono[p-(1,1,3,3-tetramethylbutyl) phenyl]ether), CHAPS (3-[(3-chloroamidepropyl)diethylammonio]propane-sulfonic acid), CHAPSO (3-[(3-chloroamidepropyl)dimethylammonio]-2-hydroxypropane-sulfonic acid), BIGCHAP (N,N-bis(3-D-gluconamidepropyl)chloramide), dioxy-BIGCHAP (N,N-bis(3-D-gluconamidepropyl) dioxychloramide), sucrose monocaprate, sucrose monocholate, n-octyl-α-D-glucopyranoside, n-heptyl-α-D-thioglucopyranoside, n-octyl-α-D-thioglupyranoside, n-dodecyl-α-D-maltopyranoside, n-nonyl-α-D-thiomaltopyranoside, and the like.

Although a sheath fluid and dilution solution are used as the washing solution in the above described embodiment, purified water may be used instead of the sheath fluid.

Water such as purified water, and solvent mixtures such as water and alcohols such as ethanol, methanol, and the like may also be used as the solvent.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A sample analyzer for analyzing a sample, comprising:
   a sample preparation unit comprising a pipette, and configured for preparing a diluted sample for measurement by diluting the sample supplied by the pipette;
   a solution container holder for holding a solution container comprising an acidic solution used for the diluting of the sample by the sample preparation unit and for washing the pipette;
   a detection unit for obtaining a detection signal from the diluted sample prepared by the sample preparation unit;

a controller in communication with the detection unit and the sample preparation unit and configured for obtaining an analysis result from the detection signal obtained by the detection unit; and a washing solution supplier for supplying a washing solution having a pH that is higher than a pH of the acidic solution;

wherein the sample preparation unit prepares the diluted sample by diluting the sample supplied by the pipette with the acidic solution suctioned from the solution container, and washes inside of the pipette by suctioning the acidic solution into the pipette from the solution container when the analysis result is equal to or greater than a predetermined value; and wherein the washing solution supplier washes outside of the pipette by supplying the washing solution.

2. The sample analyzer of claim 1, wherein the sample preparation unit washes the pipette by supplying the washing solution into the pipette from the washing solution supplier and then, when the analysis result is equal to or greater than the predetermined value, further washes the pipette by suctioning the acidic solution into the pipette from the solution container.

3. The sample analyzer of claim 1, wherein the sample preparation unit washes the pipette by suctioning the acidic solution into the pipette from the solution container and discharging the suctioned acidic solution from the pipette.

4. The sample analyzer of claim 1, wherein the sample preparation unit washes the pipette by holding the suctioned acidic solution within the pipette for a predetermined time.

5. The sample analyzer of claim 1, wherein the controller calculates number of bacteria contained in the sample.

6. The sample analyzer of claim 1, wherein the acidic solution has a pH of less than 5.0.

7. The sample analyzer of claim 1, wherein the acidic solution has a pH of between 2 and 3.

8. A bacteria analyzer for analyzing a bacterium in a sample, comprising:

a sample preparation unit comprising a pipette and configured for preparing an assay sample for measurement from the sample supplied by the pipette;

a solution container holder for holding a solution container comprising an acidic solution used for washing the pipette;

a detection unit for obtaining a detection signal relating to a bacterium from the assay sample prepared by the sample preparation unit;

a controller in communication with the detection unit and the sample preparation unit and configured for obtaining an analysis result relating to a bacterium in the sample from the detection signal obtained by the detection unit; and a washing solution supplier for supplying a washing solution having a pH that is higher than a pH of the acidic solution;

wherein the sample preparation unit washes inside of the pipette by suctioning the acidic solution into the pipette from the solution container when the analysis result is equal to or greater than a predetermined value; and wherein the washing solution supplier washes outside of the pipette by supplying the washing solution.

9. The bacteria analyzer of claim 8, wherein the sample preparation unit prepares the assay sample by diluting the sample with a dilution fluid to form a diluted sample, and staining the diluted sample with a stain.

10. The bacteria analyzer of claim 9, wherein the acidic solution is used as the dilution fluid.

11. The bacteria analyzer of claim 9, wherein the dilution fluid is used for destroying a membrane of the bacterium for effective staining of the bacterium.

12. The bacteria analyzer of claim 8, wherein the sample comprises urine.

13. A urine analyzer for analyzing a urine sample, comprising:

a sample preparation unit comprising a pipette and configured for preparing a diluted urine sample for measurement by diluting the urine sample supplied by the pipette;

a solution container holder for holding a solution container comprising an acidic solution used for the diluting of the urine sample by the sample preparation unit and for washing the pipette;

a detection unit for obtaining a detection signal from the diluted urine sample prepared by the sample preparation unit;

a controller in communication with the detection unit and the sample preparation unit and configured for obtaining an analysis result from the detection signal obtained by the detection unit; and a washing solution supplier for supplying a washing solution having a pH that is higher than a pH of the acidic solution;

wherein the sample preparation unit prepares the diluted urine sample by diluting the urine sample supplied by the pipette with the acidic solution suctioned from the solution container, and washes inside of the pipette by suctioning the acidic solution into the pipette from the solution container when the analysis result is equal to or greater than a predetermined value; and wherein the washing solution supplier washes outside of the pipette by supplying the washing solution.

14. The sample analyzer of claim 1, further comprising a sheath fluid supplier for supplying a sheath fluid to the detection unit to form a sheath flow.

15. A sample analyzer for analyzing a sample, comprising:

a sample preparation unit comprising a pipette and configured for preparing a diluted sample for measurement by diluting the sample supplied by the pipette;

a solution container holder;

a solution container comprising an acidic solution used for the diluting of the sample by the sample preparation unit and for washing the pipette;

a detection unit for obtaining a detection signal from the diluted sample prepared by the sample preparation unit;

a controller in communication with the detection unit and the sample preparation unit and configured for obtaining an analysis result from the detection signal obtained by the detection unit; and a washing solution supplier for supplying a washing solution having a pH that is higher than a pH of the acidic solution;

wherein the sample preparation unit prepares the diluted sample by diluting the sample supplied by the pipette with the acidic solution suctioned from the solution container, and washes inside of the pipette by suctioning the acidic solution into the pipette from the solution container when the analysis result is equal to or greater than a predetermined value; and wherein the washing solution supplier washes outside of the pipette by supplying the washing solution.

* * * * *

UNITED STATES PATENT AND TRADEMARK OFFICE
CERTIFICATE OF CORRECTION

| | | |
|---|---|---|
| PATENT NO. | : 7,662,631 B2 | |
| APPLICATION NO. | : 10/692554 | |
| DATED | : February 16, 2010 | |
| INVENTOR(S) | : Kawashima et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 603 days.

Signed and Sealed this

Twenty-eighth Day of December, 2010

David J. Kappos
*Director of the United States Patent and Trademark Office*